United States Patent
Zhang et al.

(10) Patent No.: US 10,603,077 B2
(45) Date of Patent: *Mar. 31, 2020

(54) ORTHOPEDIC FASTENER FOR STABILIZATION AND FIXATION

(75) Inventors: Hong Zhang, Plano, TX (US); Dan Sucato, Dallas, TX (US)

(73) Assignee: Globus Medical, Inc., Audubon, PA (US)

( * ) Notice: Subject to any disclaimer, the term of this patent is extended or adjusted under 35 U.S.C. 154(b) by 1816 days.

This patent is subject to a terminal disclaimer.

(21) Appl. No.: 12/101,752

(22) Filed: Apr. 11, 2008

(65) Prior Publication Data

US 2008/0269810 A1 Oct. 30, 2008

Related U.S. Application Data

(60) Provisional application No. 60/911,468, filed on Apr. 12, 2007.

(51) Int. Cl.
*A61B 17/70* (2006.01)
*A61F 2/44* (2006.01)
*A61B 90/00* (2016.01)

(52) U.S. Cl.
CPC ........ *A61B 17/701* (2013.01); *A61B 17/7001* (2013.01); *A61B 17/7034* (2013.01);
(Continued)

(58) Field of Classification Search
CPC .............. A61B 17/7034; A61B 17/701; A61B 17/7032; A61F 2/44
(Continued)

(56) References Cited

U.S. PATENT DOCUMENTS 4,422,451 A * 12/1983 Kalamchi .......... A61B 17/7002
606/207
4,653,489 A 3/1987 Tronzo
(Continued)

FOREIGN PATENT DOCUMENTS

JP 2003250822 A 9/2003
WO 2008128105 A1 10/2008
(Continued)

OTHER PUBLICATIONS

International Search Report and Written Opinion for PCT/US2008/060115 dated Sep. 18, 2008.
(Continued)

*Primary Examiner* — Bruce E Snow
*Assistant Examiner* — Melissa A Hoban

(57) ABSTRACT

The present invention includes an apparatus, kit and method for providing a bone fixation assembly for attachment to a bone to provide augmented support. The bone fixation assembly includes a screw having a screw head and a threaded shank. A first aperture is positioned about the screw head to receive a first longitudinal member and a first compression member that engages the first aperture to secure the first longitudinal member. The screw head has a second aperture positioned to receive a second longitudinal member and a second compression member that engages the second longitudinal member aperture to secure the second longitudinal member and provide augmented support.

19 Claims, 15 Drawing Sheets

(52) U.S. Cl.
CPC .... *A61B 17/7037* (2013.01); *A61B 2090/037* (2016.02); *A61F 2/44* (2013.01)

(58) Field of Classification Search
USPC .................................... 606/305; 623/16.11
See application file for complete search history.

(56) References Cited

U.S. PATENT DOCUMENTS

| | | | |
|---|---|---|---|
| 4,743,260 A | 5/1988 | Burton | |
| 4,772,261 A | 9/1988 | Von Hoff et al. | |
| 4,946,458 A | 8/1990 | Harms et al. | |
| 5,005,562 A | 4/1991 | Cotrel | |
| 5,047,030 A | 9/1991 | Draenert | |
| 5,067,955 A | 11/1991 | Cotrel | |
| 5,122,131 A * | 6/1992 | Tsou ................ | A61B 17/7032 606/328 |
| 5,129,349 A | 7/1992 | Glen | |
| 5,133,717 A | 7/1992 | Chopin | |
| 5,176,678 A * | 1/1993 | Tsou ................ | A61B 17/7032 606/267 |
| 5,207,678 A * | 5/1993 | Harms .............. | A61B 17/7008 606/267 |
| 5,219,349 A | 6/1993 | Krag et al. | |
| 5,281,222 A * | 1/1994 | Allard ............... | A61B 17/7032 606/264 |
| 5,329,933 A | 7/1994 | Graf | |
| 5,385,565 A | 1/1995 | Ray | |
| 5,397,363 A | 3/1995 | Gelbard | |
| 5,593,407 A | 1/1997 | Reis | |
| 5,603,714 A * | 2/1997 | Kaneda ............ | A61B 17/7034 606/272 |
| 5,609,593 A * | 3/1997 | Errico .............. | A61B 17/7037 606/266 |
| 5,620,443 A * | 4/1997 | Gertzbein et al. ........ | 606/252 |
| 5,630,816 A | 5/1997 | Kambin | |
| 5,653,708 A * | 8/1997 | Howland ........... | A61B 17/7055 606/264 |
| 5,702,392 A * | 12/1997 | Wu .................. | A61B 17/7008 606/250 |
| 5,702,395 A | 12/1997 | Hopf | |
| 5,707,372 A | 1/1998 | Errico et al. | |
| 5,728,097 A | 3/1998 | Mathews | |
| 5,800,407 A | 9/1998 | Eldor | |
| 5,871,484 A | 2/1999 | Spievack et al. | |
| 5,876,403 A | 3/1999 | Shitoto | |
| 5,993,449 A * | 11/1999 | Schlapfer et al. ......... | 606/60 |
| 6,077,263 A | 6/2000 | Ameil et al. | |
| 6,090,113 A | 7/2000 | Le Couedic et al. | |
| 6,136,002 A * | 10/2000 | Shih et al. ............ | 606/250 |
| 6,214,012 B1 | 4/2001 | Karpman et al. | |
| 6,248,106 B1 | 6/2001 | Ferree | |
| 6,287,309 B1 | 9/2001 | Baccelli et al. | |
| 6,342,054 B1 * | 1/2002 | Mata ................. | A61B 17/62 606/54 |
| 6,423,062 B2 | 7/2002 | Enayati | |
| 6,461,359 B1 | 10/2002 | Tribus et al. | |
| 6,488,681 B2 | 12/2002 | Martin et al. | |
| 6,517,542 B1 | 2/2003 | Papay et al. | |
| 6,554,830 B1 | 4/2003 | Chappius | |
| 6,554,834 B1 | 4/2003 | Crozet et al. | |
| 6,558,390 B2 | 5/2003 | Cragg | |
| 6,565,572 B2 | 5/2003 | Chappius | |
| 6,569,164 B1 | 5/2003 | Assaker et al. | |
| 6,582,439 B1 | 6/2003 | Sproul | |
| 6,610,063 B2 | 8/2003 | Kumar et al. | |
| 6,620,195 B2 | 9/2003 | Goble et al. | |
| 6,623,485 B2 | 9/2003 | Doubler et al. | |
| 6,663,637 B2 | 12/2003 | Dixon et al. | |
| 6,730,095 B2 | 5/2004 | Olson, Jr. et al. | |
| 6,740,086 B2 | 5/2004 | Richelsoph | |
| 6,740,090 B1 | 5/2004 | Cragg et al. | |
| 6,749,613 B1 | 6/2004 | Conchy et al. | |
| 6,755,835 B2 | 6/2004 | Schultheiss et al. | |
| 6,780,191 B2 | 8/2004 | Sproul | |
| 6,858,030 B2 | 2/2005 | Martin et al. | |
| 6,881,215 B2 | 4/2005 | Assaker et al. | |
| 6,899,714 B2 | 5/2005 | Vaughan | |
| 6,942,698 B1 | 9/2005 | Jackson | |
| 6,964,665 B2 | 11/2005 | Thomas et al. | |
| 6,974,460 B2 | 12/2005 | Carbone et al. | |
| 6,976,988 B2 | 12/2005 | Ralph et al. | |
| 6,981,973 B2 | 1/2006 | McKinley | |
| 7,008,433 B2 | 3/2006 | Voellmicke et al. | |
| 7,033,392 B2 | 4/2006 | Schmiel et al. | |
| 7,041,138 B2 | 5/2006 | Lange | |
| 7,163,539 B2 | 1/2007 | Abdelgany et al. | |
| 7,220,262 B1 | 5/2007 | Hynes | |
| 7,658,753 B2 | 2/2010 | Carl et al. | |
| 7,776,072 B2 | 8/2010 | Barry | |
| 7,789,897 B2 | 9/2010 | Sanders | |
| 8,007,522 B2 | 8/2011 | Hutchinson | |
| 8,083,773 B2 | 12/2011 | Durrani | |
| 8,206,388 B2 * | 6/2012 | Thomke ............ | A61B 17/6466 606/324 |
| 8,277,453 B2 | 10/2012 | Kave et al. | |
| 2002/0007183 A1 | 1/2002 | Lee et al. | |
| 2002/0013585 A1 | 1/2002 | Gournay et al. | |
| 2002/0095153 A1 | 7/2002 | Jones et al. | |
| 2003/0065329 A1 | 4/2003 | Vaughan | |
| 2003/0144664 A1 | 7/2003 | Cavagna et al. | |
| 2004/0039383 A1 * | 2/2004 | Jackson ............ | A61B 17/7032 606/270 |
| 2004/0111088 A1 | 6/2004 | Picetti et al. | |
| 2004/0158247 A1 | 8/2004 | Sitiso et al. | |
| 2005/0203511 A1 | 9/2005 | Wilson-MacDonald et al. | |
| 2005/0234449 A1 | 10/2005 | Aferzon | |
| 2005/0277934 A1 | 12/2005 | Vardiman | |
| 2006/0036246 A1 | 2/2006 | Carl et al. | |
| 2006/0173456 A1 | 8/2006 | Hawkes et al. | |
| 2006/0195092 A1 | 8/2006 | Barry | |
| 2006/0249623 A1 | 11/2006 | Anderson et al. | |
| 2006/0293659 A1 | 12/2006 | Alvarez | |
| 2007/0093824 A1 | 4/2007 | Hestad et al. | |
| 2007/0213715 A1 | 9/2007 | Bridwell et al. | |
| 2007/0213716 A1 | 9/2007 | Lenke et al. | |
| 2007/0225713 A1 | 9/2007 | Altarac et al. | |
| 2007/0233062 A1 | 10/2007 | Berry | |
| 2007/0233089 A1 | 10/2007 | Dipoto et al. | |
| 2007/0270805 A1 * | 11/2007 | Miller et al. ................... | 606/61 |
| 2007/0270810 A1 | 11/2007 | Sanders | |
| 2007/0286366 A1 | 12/2007 | Deboy et al. | |
| 2008/0027436 A1 | 1/2008 | Cournoyer et al. | |
| 2008/0177323 A1 | 7/2008 | Null et al. | |
| 2008/0255617 A1 | 10/2008 | Cho et al. | |
| 2009/0099605 A1 | 4/2009 | Fallin et al. | |
| 2009/0131982 A1 | 5/2009 | Schwab | |
| 2009/0198273 A1 | 8/2009 | Zhang et al. | |
| 2009/0198279 A1 | 8/2009 | Zhang et al. | |
| 2009/0326586 A1 | 12/2009 | Duarte | |
| 2010/0042149 A1 | 2/2010 | Chao et al. | |
| 2010/0076494 A1 | 3/2010 | Markworth | |
| 2010/0249843 A1 | 9/2010 | Wegrzyn, III | |
| 2010/0256683 A1 | 10/2010 | Iott et al. | |
| 2011/0137358 A1 | 6/2011 | Manninen | |
| 2012/0221057 A1 | 8/2012 | Zhang et al. | |
| 2013/0090691 A1 | 4/2013 | Zhang et al. | |

FOREIGN PATENT DOCUMENTS

| | | |
|---|---|---|
| WO | 2009097623 A2 | 8/2009 |
| WO | 2009097624 A2 | 8/2009 |

OTHER PUBLICATIONS

Berguiristain, J. L., et al., "Experimental Scoliosis by Epiphysiodesis in Pigs," International Orthopaedics (1980), 3:317-321.

Bradford, D.S., et al., "One-stage anterior and posterior hemivertebral resection and arthrodesis for congenital scoliosis." JBJS (1990), 72-A:536-40.

Compere, E.L., et al., "Excision of hemivertebrae for correction of congenital scoliois: report of two cases." JBJS (1932), 14-A:555-62.

(56) References Cited

OTHER PUBLICATIONS

Deviren, V., et al. "Excision of hemivertebrae in the management of congenital scoliosis involving the thoracic and thoracolumbar spine." JBJS (2001), 83-B:496-500.
Floman, Y., et al. "Osteotomy of the fusion mass in scoliosis." JBJS (1982), 64-A:1307-16.
Leatherman, K.D., et al. "Two-stage corrective surgery for congenital deformities of the spine." JBJS (1979), 61-B:324-8.
Suk, S., et al. "Posterior vertebral column resection for severe spinal deformities." Spine (2002), 27:2374-82.
Suk, S., et al. "Posterior vertebral column resection for severe spinal deformities." Spine (2005), 30:1682-87.
Suk, S., et al. "Posterior vertebral column resection in fixed lumbosacral deformity." Spine (2005), 30:E703-10.
Tokunaga, M., et al. "Verteral decancellation for severe scoliosis." Spine (2000), 25:469-74.
Wiles, P. "Resection of dorsalvertebrae in congenital scoliosis." JBJS (1951), 33-A:151-4.
International Search Report and Written Opinion of KIPO for PCT/US2009/032901 dated Sep. 24, 2009, 9 pages.
International Search Report and Written Opinion of KIPO for PCT/US2009/032899 dated Oct. 15, 2009, 13 pages.
International Search Report and Written Opinion of Australia Patent Office for PCT/US2008/60115 dated Sep. 18, 2008, 9 pages.

\* cited by examiner

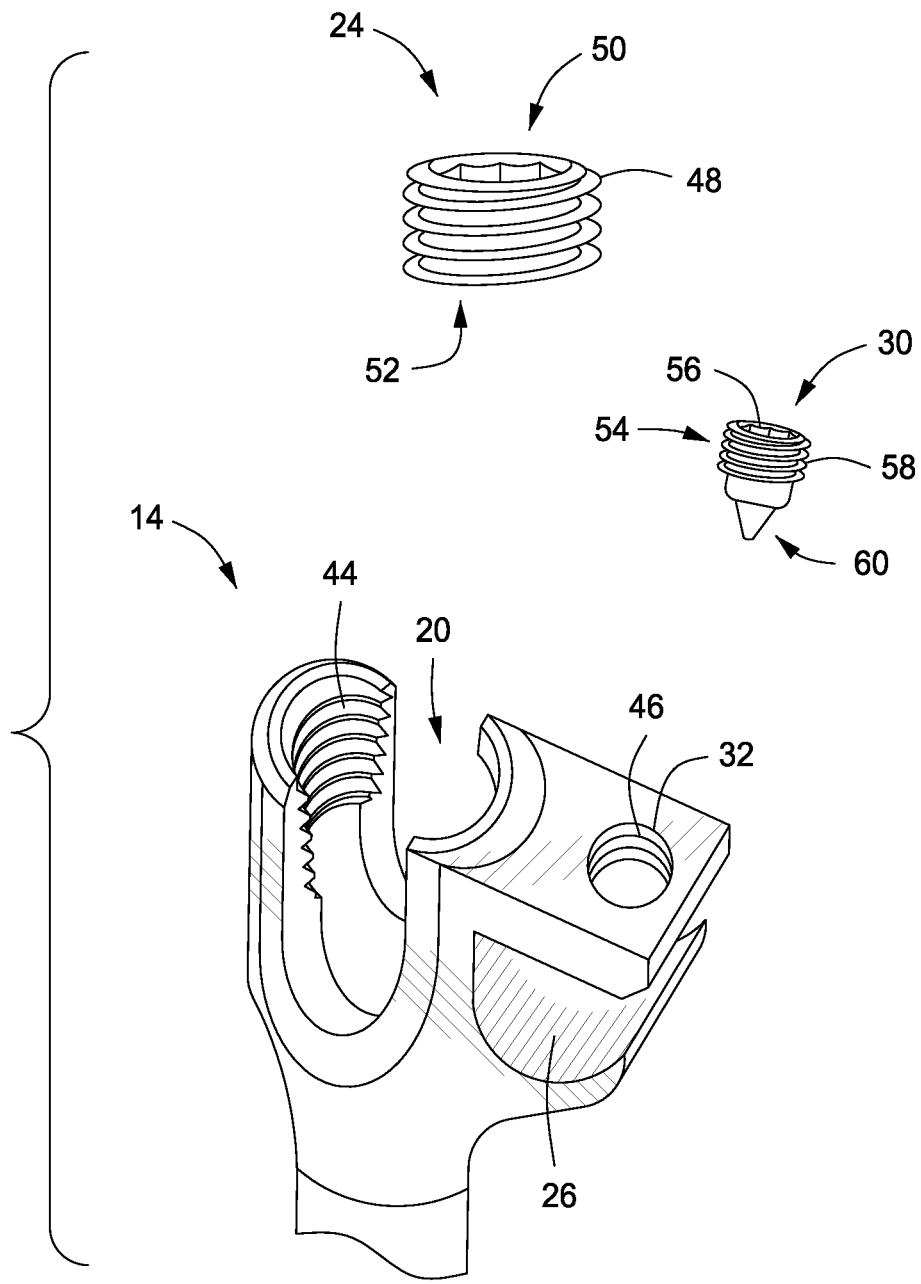

ORTHOPEDIC FASTENER FOR STABILIZATION AND FIXATION

CROSS-REFERENCE TO RELATED APPLICATIONS

This application claims priority to U.S. Provisional Application Ser. No. 60/911,468 filed on Apr. 12, 2007, the contents of which is incorporated by reference herein in its entirety.

TECHNICAL FIELD OF THE INVENTION

The present invention relates in general to the field of fasteners and fastening methods for use in orthopedic surgery, and more particularly, to fasteners and fastening methods for stabilization and fixation of, e.g., vertebra, using a subcutaneous orthopedic assembly.

BACKGROUND OF THE INVENTION

Without limiting the scope of the invention, its background is described in connection with spinal fixation assemblies to align vertebral bodies, as an example.

The successive positioning of the vertebral body allows the vertebral foramen to surround the spinal cord, retain articulation of the vertebrae and extend posteriorly of the spinal canal. The complicated vertebral structure, the degree of spinal articulation and the complicated network of connective elements make the spine susceptible to many forms of damage, e.g., traumatic spinal injuries, tumors, infections, surgeries, disease processes, aging processes and congenital abnormalities. Various types of spinal column disorders are known and include degenerative disc disease, excess lordosis (abnormal backward curvature of the spine), fractured vertebra, kyphosis (abnormal forward curvature of the spine), ruptured discs, scoliosis (abnormal lateral curvature of the spine), slipped discs, spondylolisthesis (abnormal forward displacement of vertebra) and the like.

Bones may be damaged (i.e., fractured) as a result of accidents (e.g., long bone fractures being the most common) or severed during a surgical procedure. The bone portions must be held together and stabilized from movement to allow bonding and recalcification. Due to the variation in the size, shape and location of the bone and to account for different function and load requirements, many different types of stabilization devices have been developed. In order to limit the movement of the bone plates, screws and pins are often used. Common internal fixation devices include wires, intramedullary pins, rods, wiring, plates, screws, bone fasteners and elongated implants (e.g., nails, screws, pins, etc.). Bone fasteners are commonly used to stabilize portions of the spine. Bone fasteners are inserted in the pedicles of a vertebra and used in conjunction with rods or plates to stabilize the spine. Generally, an incision into the tissue surrounding the bone and the bone portions are clamped together so that holes may be drilled into the bone. Pins or screws are then inserted through the holes to secure the bones. A cast or splint is added to further reduce the movement and mechanical strain on the bone that may cause bone separation.

Generally, spinal fixation assemblies are used to position the vertebrae in a desired spatial relationship for treatment, e.g., healing, spinal fusion, support and so forth. Spinal fixation assemblies include spinal fixation elements commonly anchored to the vertebrae via pedicle screws that extend through the pedicle into the vertebral bodies or by spinal hooks that engage about the vertebrae. The spinal fixation elements are coupled together with relatively rigid fixation rods by generally yoke-shaped couplers that can be either integral with the spinal fixation element or separate components from the spinal fixation element. The spinal fixation elements are secured relative to the fixation rod by a compression member that is engages either directly or indirectly the fixation rod. The fixation rods are secured to maintain the alignment and position of the vertebral bodies.

For example, one such method of orthopedic fixation is taught in U.S. Pat. No. 5,005,562 issued to Cotrel, and incorporated herein by reference, which teaches an implant for a spinal osteosynthesis device, in particular in traumatology. The implant includes a body having a channel defining two side branches that are open on both sides of the body in order to be able to receive a rod, and a threaded plug contrived so that it can be screwed into a female thread formed in the inner walls of the two branches so that its two diametrically opposed edges bear on the rod and the face of the plug directed towards the rod, which can thus be clamped in translation and rotation.

Another such method of orthopedic fixation is taught in U.S. Pat. No. 6,623,485 issued to Doubler, et al., which teaches a split ring bone screw for a spinal fixation system. The adjustable spinal fixation system includes anchoring assemblies attached to spine-stabilizing rods. The anchoring assemblies include a linking member attached in a ball-and-socket fashion to a bone-engaging member that is adapted to engage a spinal bone of a patient. The linking member joins one of the included connectors to an associated bone-engaging member. The connectors are attached selectively to one of the stabilizing rods. The anchoring assemblies each include a support collar and a split retention ring that cooperate to allow adjustment of the bone-engaging member and corresponding connector during surgery. When surgery is complete, a securing nut and locking bolt cooperate with the support collar and split retention ring to maintain the relative position of the entire fixation system, preventing unwanted movement between the system components.

An orthopedic fixation is taught in U.S. Pat. No. 6,610,063 issued to Kumar, et al., which teaches a spinal fixation system that is particularly useful in treatment of pediatric and small-statured patients. The fastener assembly includes a fastener, an attachment member and a locking member. The fastener has a lower portion for contacting a bone and an upper portion integral with the lower portion and having two open channels. Each channel is configured and dimensioned for receiving a portion of the longitudinal member along its circumference. The attachment member is positionable on the fastener and at least partially covers the channel that receives the longitudinal member. The attachment member is configured and dimensioned for receiving another portion of the longitudinal member along its circumference. The locking member is operatively associated with the upper portion of the fastener and secures the attachment member and longitudinal member to the fastener.

Another such method of orthopedic fixation is taught in U.S. Pat. No. 6,945,975 issued to Dalton, which teaches a bone plate for fixation of spaced vertebra. The bone plate has at least one through passage for securing the plate to bone with a bone fixation screw. The threaded shaft of a bone fixation screw is inserted through a bushing located in the through passage of the bone plate and the screw is thereby threadably secured to the underlying bone. Next, the bushing is compressed inward against the head of the screw with cams that are actuated by rotating the bushing in the through passage, whereby the screw is locked relative to the bone plate. The bushing is not only compressed inwardly against the head of the screw but is also compressed downwardly by the cams into a seat to clamp separate elements of the bone plate together.

Another approach is the orthopedic fixation taught in U.S. Pat. No. 6,248,106 issued to Ferree, which teaches a spinal stabilization mechanism that acts to prevent lateral bending, extension and rotation at the disc space. The patent teaches two or more anchors at each vertebral level and links at each vertebral level to both anchors at the other vertebral level resulting in a cross-braced arrangement that enhances compression and promotes fusion.

In addition, a flexible stabilization system for a vertebral column is taught in U.S. Pat. No. 4,743,260, issued to Burton, which teaches a device that includes a strong, non-metallic stabilization element or elements for providing flexibility. The stabilization elements are secured to the vertebrae to stabilize the vertical column while still allowing for flexibility. The stabilization elements are anchored to the vertebrae by a bone screw having an upper shank portion and a lower threaded portion having a segmented area.

In some instances, there is a need for a spinal fixation assembly that provides a stronger and/or more stable spatial relationship for the vertebrae. For example, a dual fixation rod assembly can be both strengthened and stabilized by the addition of a cross-brace that extends across the spine to couple the two fixation rods. This is seen when the two fixation rods are geometrically aligned, i.e., the two rods are parallel. However, in clinical situations, the two fixation rods are rarely three-dimensionally geometrically aligned and are bent to accommodate the alignment, e.g., bending one or both of the two fixation rods and/or the cross-brace. The bending can adversely affect the fixation to the spine and adversely affect the mechanical properties of the fixation rods and/or cross-brace. Given the constrained size limitations imposed by the spinal area and the size and strength necessary for the spinal fixation assemblies, the alignment of non-coplanar rods, convergence alignments, divergence alignments and augmented spinal fixation assemblies is difficult.

The foregoing problems have been recognized for many years and while numerous solutions have been proposed, none of them adequately address all of the problems in a single device.

SUMMARY OF THE INVENTION

The present inventor recognized a need for a subcutaneous orthopedic assembly for stabilization and fixation of bones that is stable, supportive and provides a connection for multiple fixation rods while reducing pain, discomfort, cost and the number and space of components associated with open procedures.

A method, apparatus and kit are provided that stabilize fractured bones by securing the bone with anchoring devices. More particularly, the present invention includes a bone fixation assembly for alignment and stabilization of vertebrae. The fastener includes a threaded shank for insertion into the bone and a screw head having a first aperture and a second aperture. The first aperture has a basic "U" shape that extends from the top of the screw head and is open on both sides of the screw head to receive a first longitudinal member and a set of female threads formed in the inner walls of the first aperture. A first compression member screwably engages the set of female threads of the first aperture and the face of the first compression member contacts the first longitudinal member. The first compression member clamps the first longitudinal member against translational and rotational movement. The second aperture has a basic "C" shape that extends from one side (i.e., generally perpendicular to the first aperture) and is open on both sides of the head to receive a second longitudinal member. The second aperture also includes a second set of female threads that accommodate a second compression member that screwably engages the second set of female threads and the face of the second compression member contacts the second longitudinal member. The second compression member clamps the second longitudinal member against translational and rotational movement.

The present invention provides a bone fixation assembly that includes a screw having a screw head and a threaded shank. The screw head includes a first aperture positioned about the screw head to receive a first longitudinal member and a first compression member to engage the first aperture to secure the first longitudinal member. The screw head includes a second aperture positioned about the screw head to receive a second longitudinal member and a second compression member to engage the second longitudinal member aperture to secure the second longitudinal member.

A bone fixation assembly having augmented support is also provided by the present invention. The bone fixation assembly includes two or more bone fixation assemblies inserted into two or more bones. Each of the two or more bone fixation assemblies includes a threaded shank and a screw head with a first aperture and a second aperture. The first aperture receives a first longitudinal member and a first compression member engages the first aperture to secure the first longitudinal member therein. The second aperture receives a second longitudinal member and a second compression member engages the second aperture to secure the second longitudinal member therein.

The bone fixation assembly includes a first longitudinal member that extends through the first aperture of each of the two or more bone fixation assemblies. The bone fixation assembly includes a second longitudinal member that extends through the second aperture of the two or more bone fixation assemblies. The second longitudinal member augments the support of the first longitudinal member.

The present invention provides a bone fixation assembly kit having two or more bone fixation assemblies. Each of the two or more bone fixation assemblies includes a threaded shank and a screw head with a first aperture that receives a first longitudinal member and a first compression member. The first compression member secures the first longitudinal member into the first aperture. The second aperture receives a second longitudinal member and a second compression member, which engages the second aperture to secure the second longitudinal member therein. The bone fixation assembly kit includes a first longitudinal member to extend through the first longitudinal member aperture of the two or more bone fixation assemblies and a second longitudinal member to extend through the second longitudinal member aperture of the two or more bone fixation assemblies.

The present invention provides a method of assembling a bone screw assembly for fixation by securing two or more bone fixation assemblies to one or more bones. Each of the two or more bone fixation assemblies includes a threaded shank and a screw head. The screw head includes a first aperture that receives a first longitudinal member and a second aperture that receives a second longitudinal member. A first compression member engages the first aperture to secure the first longitudinal member therein, while a second compression member engages the second aperture to secure the second longitudinal member therein. The two or more bone fixation assemblies are aligned and the first longitudinal member is secured in the first aperture of each of the two or more bone fixation assemblies. Similarly, the second longitudinal member is secured in the second aperture of each of the two or more bone fixation assemblies.

The present invention also includes a method of constructing a platform using a fastener for attachment to an object to provide support for the platform.

BRIEF DESCRIPTION OF THE DRAWINGS

For a more complete understanding of the features and advantages of the present invention, reference is now made to the detailed description of the invention along with the accompanying figures and in which:

FIG. 4 illustrates a perspective view of a portion of the bone screw assembly of the present invention according to FIG. 1;

DETAILED DESCRIPTION OF THE INVENTION

Figure 1:
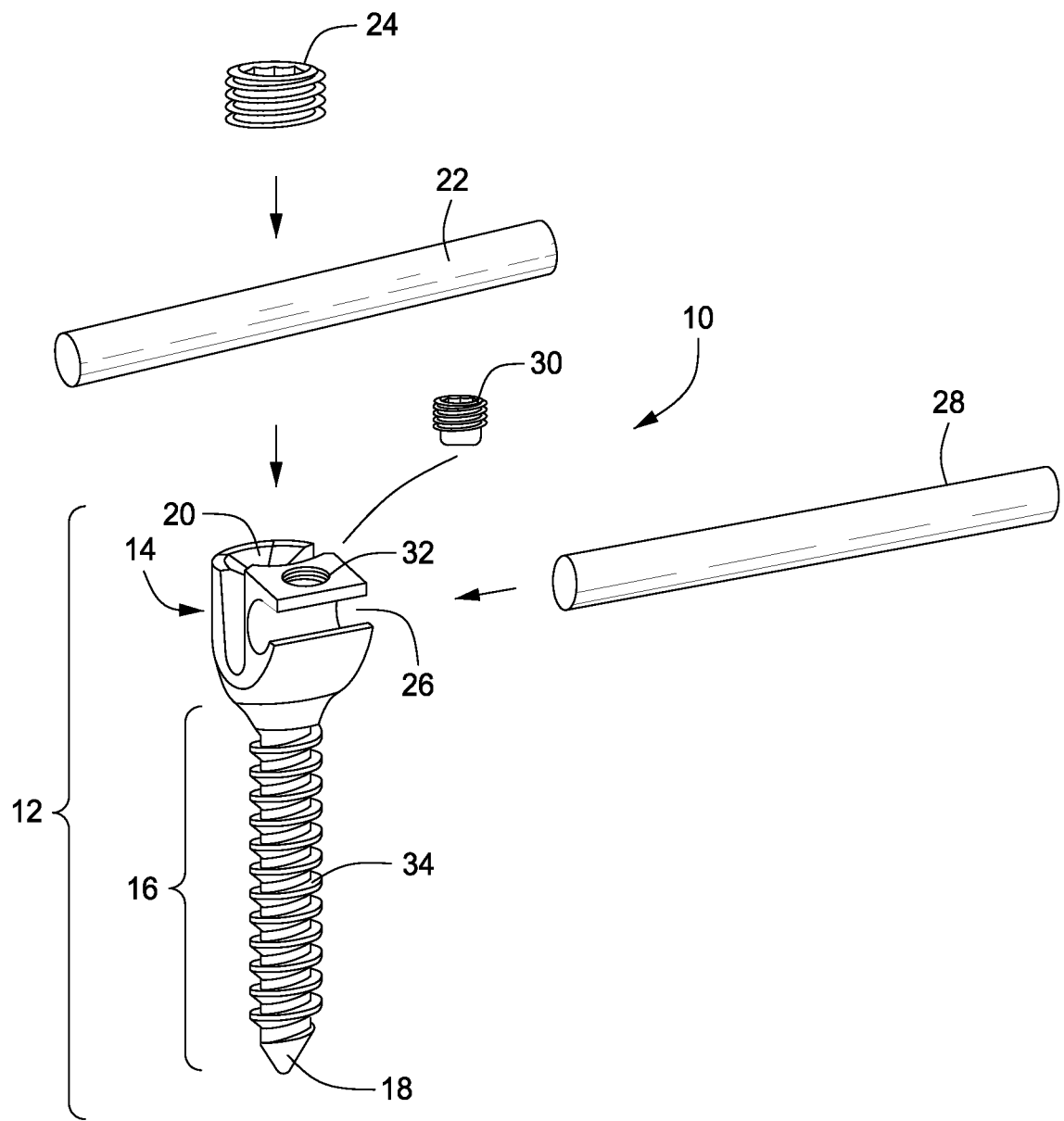
FIG. 1 illustrates an exploded view of the bone screw assembly according to an embodiment of the invention.

While the making and using of various embodiments of the present invention are discussed in detail below, it should be appreciated that the present invention provides many applicable inventive concepts that can be embodied in a wide variety of specific contexts. The terminology used and specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Generally, spinal injuries result in the displacement of all or part of one or more vertebrae from the remainder of the vertebral column. The displaced vertebrae must be repositioned to their normal position and fixed within the vertebral column. Generally, these fixation and positioning methods rely on a variety of metal wires, screws, rods, plates and clamps to stabilize the bone and/or bone fragments during the healing or fusing process.

The present invention includes a bone fixation assembly, kits and methods for the alignment and stabilization of vertebrae. The threaded shank of the bone fixation assembly is inserted into the bone with the screw head having a first aperture and a second aperture extending from the bone. The first aperture has a basic "U" shape that extends from the top of the screw head and a set of female threads formed in the inner walls of the first aperture. Once the first longitudinal member is positioned in the first aperture, a first compression member can be screwed into the set of female threads of the first aperture. The first compression member can be tightened to provide a friction fit between the surface of the first compression member, the first longitudinal member and the surface of the first aperture. The first compression member clamps the first longitudinal member against translational and rotational movement. A second longitudinal member can be placed from the lateral side into the second aperture that has a basic "C" shape that extends from one side (i.e., opening that is generally perpendicular to the first aperture) and is open on both sides. A threaded second compression member aperture extends from the top of the screw head into the second aperture.

Once a second longitudinal member is positioned in the second aperture, a second compression member can be screwed into the threaded second compression member aperture to contact the second longitudinal member. The second compression member can be tightened to provide a friction fit between the surface of the second compression member, the second longitudinal member and the surface of the second aperture. The second compression member clamps the second longitudinal member against translational and rotational movement.

Refer now to FIG. 1, an exploded view of a bone fastener assembly, generally designated by reference numeral 10, according to one embodiment of the present invention. The bone fastener assembly 10 includes a bone screw 12 having a screw head 14 connected to a shank 16 that extends to a tapered tip 18. The screw head 14 includes a first longitudinal member aperture 20 designed and proportioned to fit a first longitudinal member 22 that is secured by a first compression member 24 that fits the first longitudinal member aperture 20. The screw head 14 also includes a second longitudinal member aperture 26 designed and proportioned to fit a second longitudinal member 28 that is secured by a second compression member 30. The second compression member 30 extends through a second compression member aperture 32 and into the second longitudinal member aperture 26 to secure the second longitudinal member 28. The shank 16 of the bone screw 12 includes a threaded portion 34 having shank threads 36. The shank 16 supports and positions the screw head 14 relative to the other components of the bone fastener assembly 10 and the spinal anatomy (not shown). The threaded portion 34 secures the bone screw 12 to the bones.

Once the bone screw 12 is inserted in the spinal anatomy (not shown), the first longitudinal member 22 may be inserted into the first longitudinal member aperture 20 of the screw head 14 from top and secured by adjusting the first compression member 24 to contact the first longitudinal member 22. The second longitudinal member 28 is positioned in the second longitudinal member aperture 26 from the lateral side and secured by adjusting the second compression member 30 to contact the second longitudinal member 28.

Figure 2:
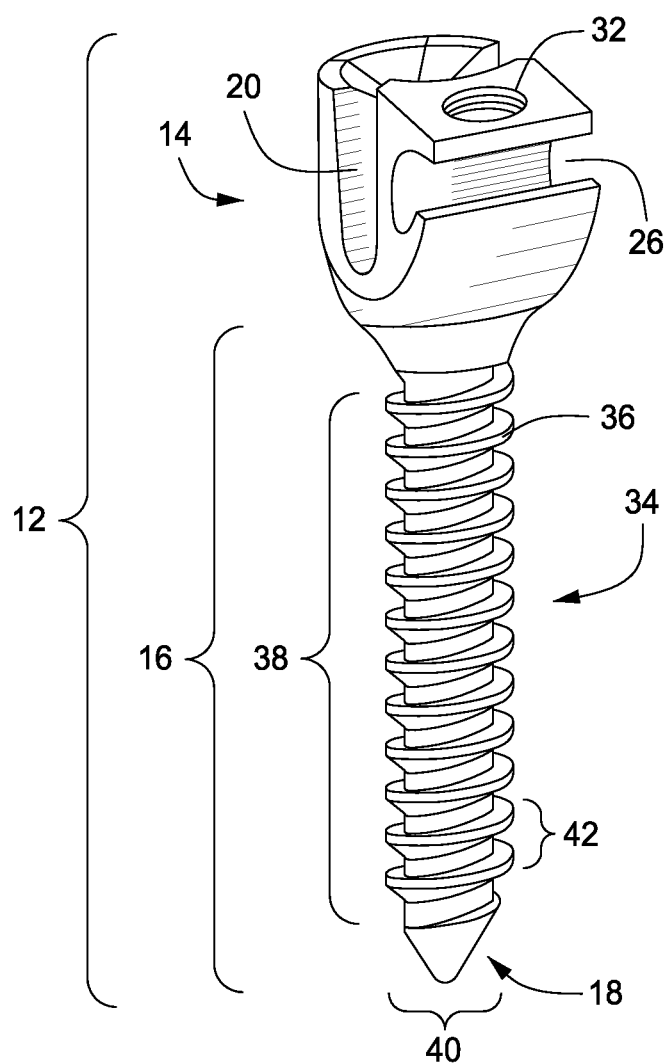
FIG. 2 illustrates a perspective view of an embodiment of the bone screw assembly of the present invention according to FIG. 1.

FIG. 2 illustrates a bone fastener assembly, generally designated by reference numeral 10, according to one embodiment of the present invention. The screw head 14 provides strength and attachment points in the form of a first longitudinal member aperture 20 and a second longitudinal member aperture 26. The first longitudinal member aperture 20 lines up superior to the shank 16. In the embodiment illustrated in FIG. 2, the shank 12 of the bone fastener assembly 10 has a threaded portion 34 having right-hand shank threads 36. The threaded portion 34 has a length 38 and a diameter 40. The threaded portion 34 may be a helical groove, a thread formed on its surface or a segmented helical member having areas with and without the helical member (not shown). In addition, the threaded portion 34 may include a non-grooved surface, e.g., regions of differing diameters as a function of length, a relatively constant diameter and so forth.

The axial distance from a point (usually the crest) on a thread to a corresponding point on an adjacent thread defines the pitch 42. The pitch 42 and the spacing of the threads of the threaded portion 34 may be varied to allow for easier insertion and/or better adhesion to the bone (not shown). The threaded portion 34 may have a different length 38, diameter 40 and/or pitch 42 as necessary for a particular purpose, particular size of bone, particular age, particular density of bone, specific vertebra, etc. The thread angle may be between 15° and 90° depending on the application. In addition, the tapered tip 18 may be sharp or blunt to allow better penetration. Additionally, the length 24, the pitch 28, the diameter 26 of the threaded portion 20 and type of threads may differ between applications.

The first longitudinal member aperture 20 and the second longitudinal member aperture 26 may be of common sizes or standard size to accept the corresponding sized first longitudinal member 22 and/or second longitudinal member 28. The first longitudinal member aperture 20 and the second longitudinal member aperture 26 may be of similar or different sizes, contours, profiles and/or shapes to accommodate first longitudinal member 22 and second longitudinal member 28 of different sizes and shapes.

The components of the present invention may be constructed from any suitable similar or dissimilar materials (e.g., titanium, a titanium alloy, a metal, an alloy, a stainless steel, a composite, a polymer, a blend of polymers, a carbon fiber, a plastic, a thermoplastic, a ceramic, carbon nanotubes, a synthetic material, a biodegradeable material or other material known to the skilled artisan) depending on the particular application or procedure. In addition, combinations and mixtures of material may be used, e.g., ceramic coated metal, carbon nanotube coated metal and/or ceramic, polymer coated metal and/or ceramic, a magnetic material combined with a polymer, metal, plastic, etc and so-forth. For example, polymers and many lightweight and/or strong materials may be used to reinforced two-phase material, carbon fiber reinforced plastic, carbon fiber, titanium coated plastic, polymers or combinations thereof.

The screws may be made of a strong material (e.g., metal, alloys, titanium, alloys, magnamite graphite fiber, carbon reinforced plastic) to prevent the screws from being sheared off by the stress of the system and remain biocompatiable. Additionally, porous material or coatings may be used to release bioactive or proactive compositions to aid in healing, promote growth, reduce infection and so forth. The materials used are not limited to the above noted and may include other suitable solid materials that have the above-noted properties.

Figure 3A:
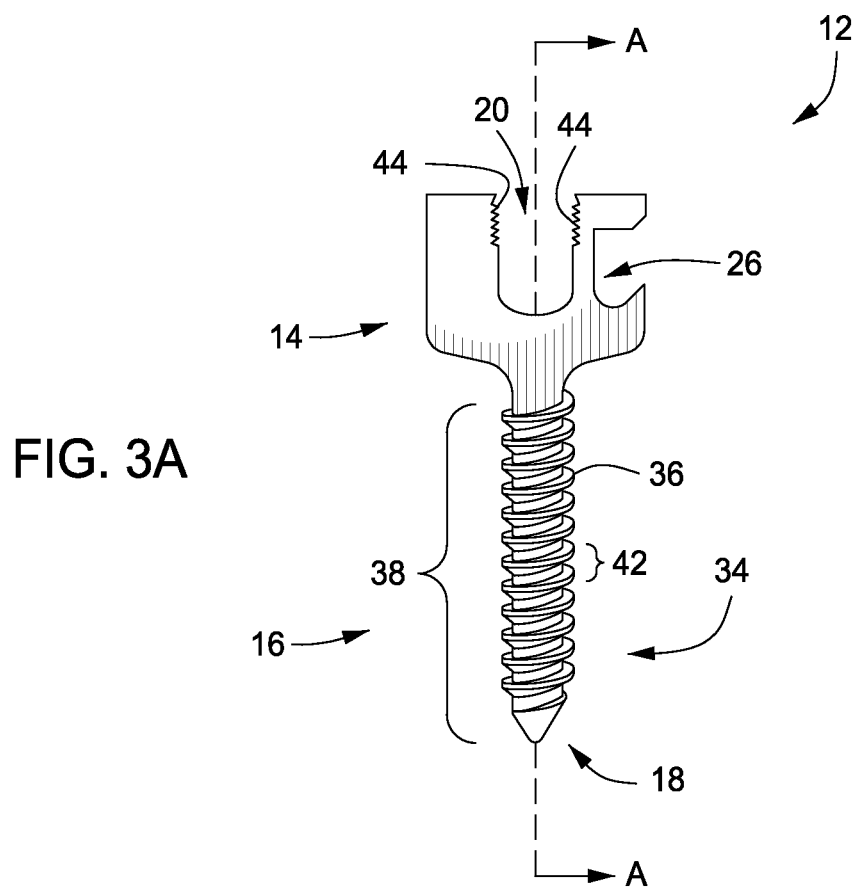
FIG. 3A illustrates a front view of an embodiment of the bone screw assembly of the present invention according to FIG. 1.

FIG. 3A illustrates a side view of the bone fastener assembly, generally designated by reference numeral 10, according to one embodiment of the present invention. The bone fastener assembly 10 includes the bone screw 12 having a screw head 14 connected to a shank 16 extending to a tapered tip 18. The screw head 14 includes a first longitudinal member aperture 20 designed and proportioned to fit a first longitudinal member (not shown). The first longitudinal member aperture 20 includes a first set of aperture threads 44 positioned about the first longitudinal member aperture 20 to accept the first compression member (not shown). The screw head 14 also includes a second longitudinal member aperture 26 designed and proportioned to fit a second longitudinal member (not shown). A second compression member (not shown) extends through a second compression member aperture (not shown) and into the second longitudinal member aperture 26 to secure the second longitudinal member (not shown). A second set of aperture treads (not shown) are positioned about the top of the screw head 14 and extend into the second longitudinal member aperture 26. The shank 16 includes a threaded portion 34 having shank threads 36 and length 38. When the bone fastener assembly is attached to a bone, it may be referred to as a bone fastener assembly.

Figure 3B:
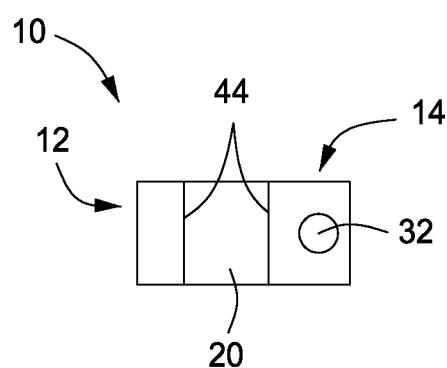
FIGS. 3B and 3C illustrate top views of different embodiment of the bone screw assembly of the present invention according to FIG. 1.
Figure 3C:
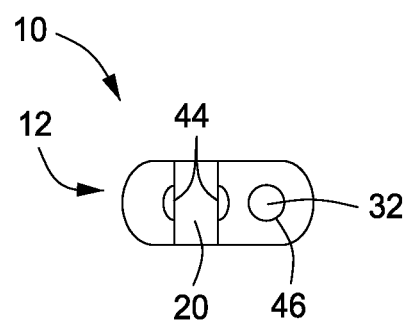

FIGS. 3B and 3C illustrate top views of the bone fastener assembly, according to different embodiment of the present invention. The bone fastener assembly 10 includes a bone screw 12 having a screw head 14 connected to a shank (not shown). The screw head 14 includes a first set of aperture threads 44 positioned on the sides of the first longitudinal member aperture 20 to accept the first compression member (not shown). The first longitudinal member aperture 20 is designed and proportioned to fit a first compression member (not shown). The screw head 14 also includes a second longitudinal member aperture (not shown) designed and proportioned to fit a second longitudinal member (not shown). The screw head 14 includes a second compression member aperture 32 having a second set of aperture threads 46 that extends into the second longitudinal member aperture (not shown).

FIG. 3B illustrates a top view of the bone fastener assembly having a screw head 14 that is rectangular in shape. FIG. 3C illustrates a top view of the bone fastener assembly having a screw head 14 that is oval in shape. The shapes illustrated in FIGS. 3B and 3C are intended as illustrations of the numerous possible screw head 14 shapes (e.g., circular, triangular, polygonal or free-formed) and combinations of shapes, e.g., one end of the screw head 14 may be circular and the other end of the screw head 14 may be triangular. Other examples of head shapes include heads that are circular-triangular, circular-polygonal, circular-square, circular-oval, triangular-polygonal, triangular-square, triangular-oval, triangular-circular, polygonal-triangular, polygonal-square, polygonal-oval, oval-polygonal, oval-square, oval-triangular, oval-polygonal and so forth.

Figure 3D:
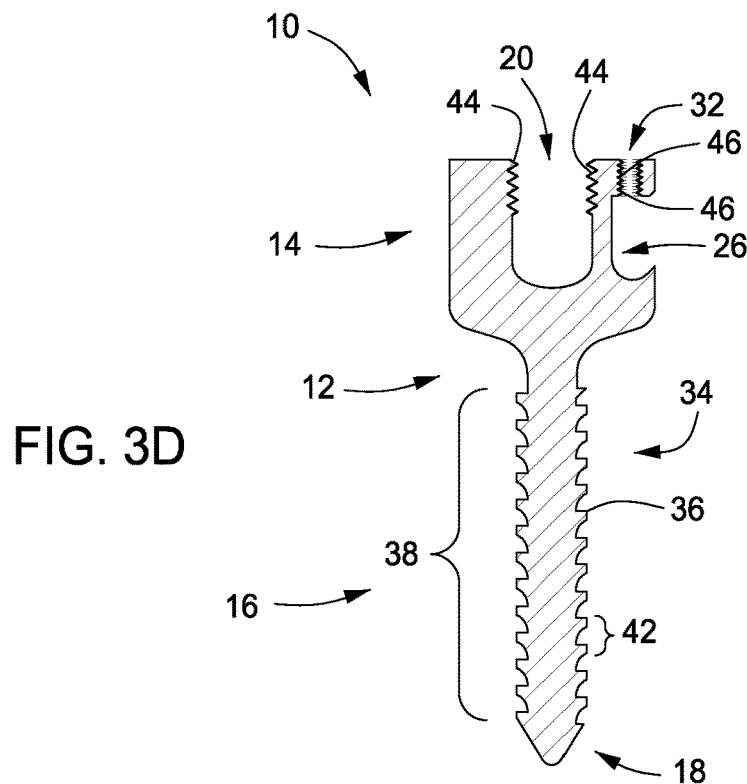
FIG. 3D illustrates a cross-sectional side view cut along section A-A of the bone screw assembly as seen in FIG. 1A according to an embodiment of the invention.

FIG. 3D illustrates a cross-sectional side view cut along section A-A of FIG. 3A. The bone fastener assembly 10 includes a bone screw 12 having a screw head 14 connected to a shank 16 extending to a tapered tip 18. The screw head 14 includes a first longitudinal member aperture 20 designed and proportioned to fit a first longitudinal member (not shown). The first longitudinal member aperture 20 includes a first set of aperture threads 44 positioned about the first longitudinal member aperture 20 to accept and secure the first compression member (not shown). The screw head 14 also includes a second longitudinal member aperture 26, which is designed and proportioned to fit a second longitudinal member (not shown). A second compression member (not shown) extends through a second compression member aperture 32 and into the second longitudinal member aperture 26 and secures the second longitudinal member (not shown). The second compression member aperture 32 has a second set of aperture treads 46 positioned about the top of the screw head 14 and extends into the second compression member aperture 32. The shank 16 includes a threaded portion 34 having shank threads 36 with a pitch 42.

Figure 3E:
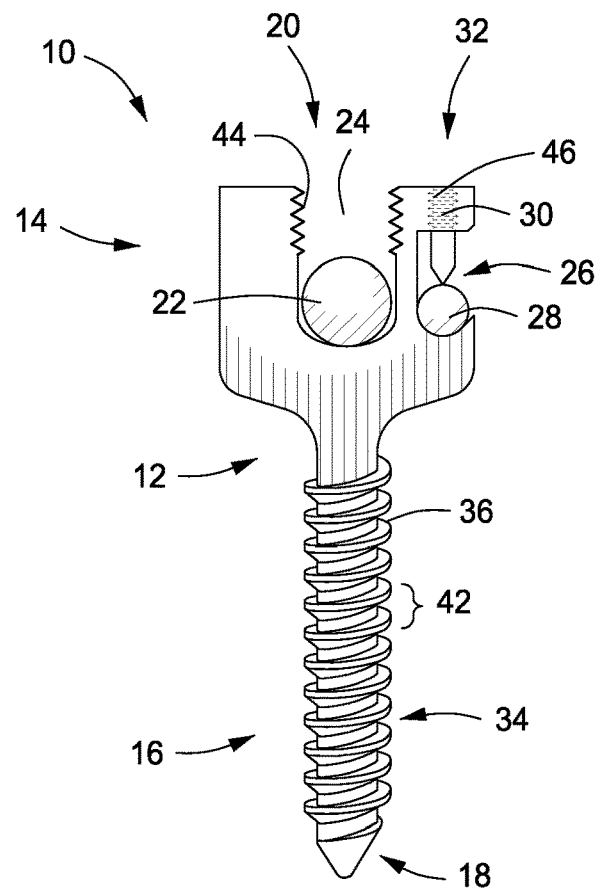
FIG. 3E illustrates a front view of an embodiment of the bone screw assembly of the present invention according to FIG. 1.

FIG. 3E illustrates a front view of the bone screw assembly, generally designated by reference numeral 10, according to one embodiment of the present invention. The bone fastener assembly 10 includes the bone screw 12 having a screw head 14 connected to a shank 16 that extends to a tapered tip 18. The screw head 14 includes a first longitudinal member aperture 20 designed and proportioned to fit a first longitudinal member 22 and a first compression member 24. The first compression member 24 secures the first longitudinal member 22 within the first longitudinal member aperture 20. The first longitudinal member aperture 20 includes a first set of aperture threads 44 positioned about the first longitudinal member aperture 20 to accept the first compression member 24. The screw head 14 also includes a second longitudinal member aperture 26 designed and proportioned to fit a second longitudinal member 28. The screw head 14 also has a second compression member aperture 32 with a second set of aperture treads 46 positioned about the top of the screw head 14 and extending into the second compression member aperture 32 and into the second longitudinal member aperture 26. A second compression member 30 extends through a second compression member aperture 32 and into the second longitudinal member aperture 26 to secure the second longitudinal member 28. The shank 16 of the bone screw 12 includes a threaded portion 34 having shank threads 36 with a pitch 42.

FIG. 4 illustrates a perspective view of the screw head 14 of the bone screw according to one embodiment of the present invention. The screw head 14 is connected to a shank (not shown). The screw head 14 provides a first longitudinal member aperture 20 and a second longitudinal member aperture 26. The first longitudinal member aperture 20 is designed and proportioned to fit a first longitudinal member (not shown). The first longitudinal member aperture 20 includes a first set of compression aperture threads 44 positioned about the first longitudinal member aperture 20 to accept the first compression member 24 and secure the first longitudinal member (not shown).

The first compression member 24 includes a first set of compression member threads 48 that mate to the first set of compression aperture threads 44. The first set of compression member threads 48 and the first set of compression aperture threads 44 have complimentary thread pitch, spacing and/or size to secure the first compression member 24 within the first longitudinal member aperture 20 and secure the first longitudinal member (not shown) within the first longitudinal member aperture 20. The first compression member 24 may be adjusted until there is no (or very little) movement of the first compression member 24 in the first longitudinal member aperture 20. The first compression member 24 includes a fitting 50 about the top that corresponds to a tool used to insert, remove, adjust, tighten or loosen the first compression member 24. The fitting may be a socket fitting, slotted fitting, Phillips fitting, Pozidriv fitting, Torx fitting, hex fitting, Robertson fitting, tri-wing fitting, Torq-set fitting, spanner fitting or specialized fitting. The size and shape of the fitting will be appropriate for the torque application. The first compression member 24 may be inserted and tightened to the appropriate position, which may protrude, resulting in the first compression member 24 being above the screw head 14, being recessed below the screw head 14 or being substantially flush with the screw head 14.

In addition, the first compression member bottom surface 52 may have a flat shape, a pointed shape, a rounded shape (e.g., concave or convex), a polygonal shape, free form shape or a combination thereof. The first compression member bottom surface 52 may be constructed from or coated with a malleable substance capable of deforming upon contact with the first longitudinal member (not shown). In addition, the first compression member 24, the first longitudinal member aperture 20, first longitudinal member 22, second longitudinal member 28, second compression member aperture 32, and/or the second compression member 30 may be in-part or entirely covered with a material or textured.

The screw head 14 also includes a second longitudinal member aperture 26 designed and proportioned to fit a second longitudinal member (not shown). The top of the screw head 14 includes a second compression member aperture 32 that extends through the screw head 14 to the second longitudinal member aperture 26. The second compression member aperture 32 includes a second set of aperture treads 46 that mate to fit a second set of compression member threads 54. The second set of compression member threads 54 and the second set of aperture treads 46 have complimentary thread pitch, spacing and/or size to secure the second compression member 30 within the second compression member aperture 32 and in turn secure the second longitudinal member (not shown) within the second longitudinal member aperture 26. The second compression member 30 is positioned into the second longitudinal member aperture 26 and adjusted to extend through a second compression member aperture 32 to contact the second longitudinal member (not shown). The second compression member 30 includes a second fitting 56 about the second compression member top surface 58 that corresponds to a tool (not shown) used to insert, remove, adjust, tighten or loosen the second compression member 30. The second compression member 30 may be adjusted to provide a friction fitting of the second compression member 30 and the second longitudinal member (not shown) to secure the second longitudinal member (not shown) and the screw head 14.

The second compression member top surface 58 may be in the shape of a pan head, button head, dome head, round head, truss head, flat head, countersunk head, bugle head, oval head, raised head, cheese head, fillister head, socket head or a combination thereof. The second fitting 56 may be a socket fitting, slotted fitting, Phillips fitting, Pozidriv fitting, Torx fitting, hex fitting, Robertson fitting, tri-wing fitting, torq-set fitting, spanner fitting or specialized fitting. The size and shape of the fitting will be appropriate for the torque application. The second compression member 30 may be inserted and tightened to the appropriate position and may protrude above the screw head 14, be recessed below the screw head 14 or be substantially flush with the screw head 14. In addition, the second compression member bottom surface 60 may have a flat shape, a pointed shape, a rounded shape (e.g., concave or convex), a polygonal shape, free-formed shape or a combination thereof. The second compression member bottom surface 60 may be constructed from or coated with a malleable substance capable of deforming upon contact with the second longitudinal member (not shown).

Figure 5:
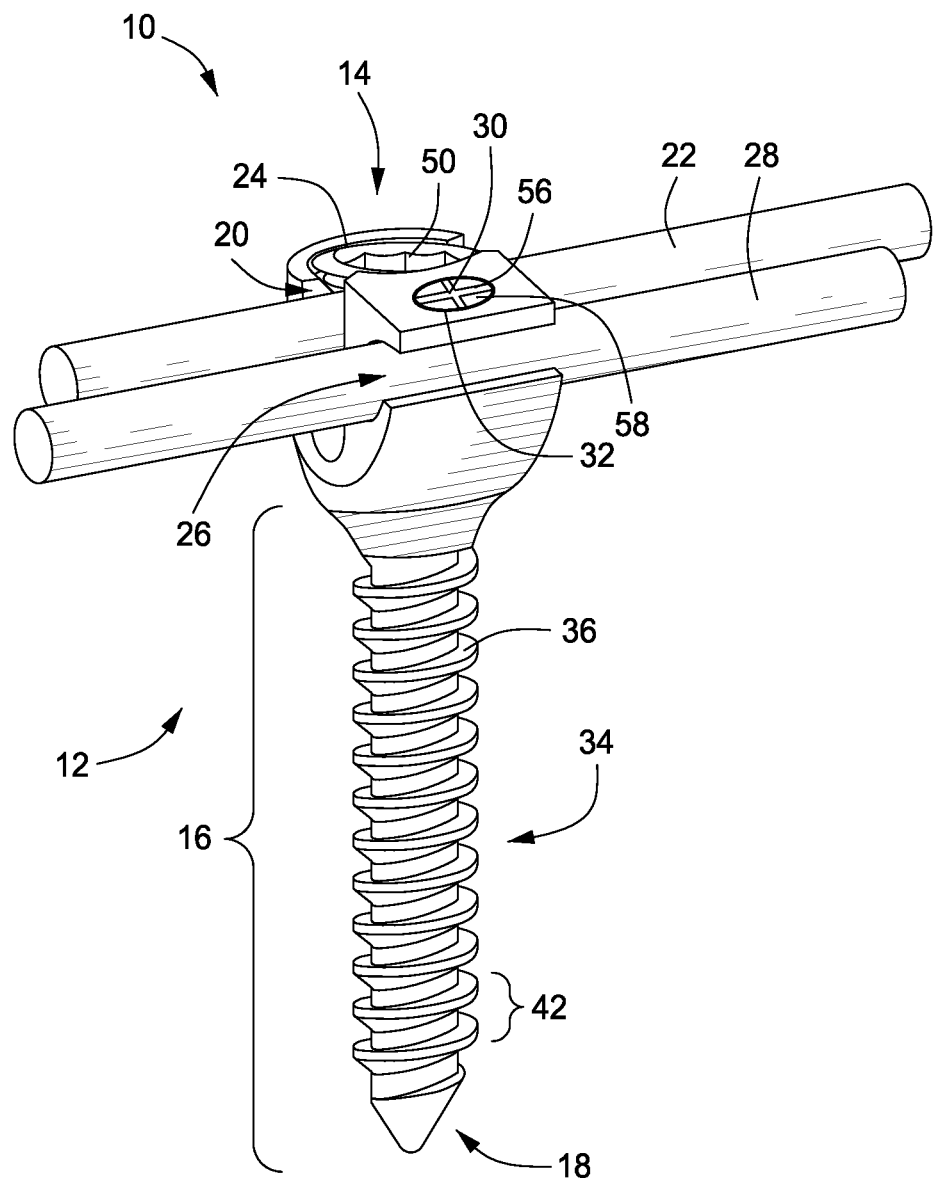
FIG. 5 illustrates a perspective view of the bone screw assembly according to an embodiment of the invention.

Refer now to FIG. 5, there being shown a bone fastener assembly, generally designated by reference numeral 10, according to one embodiment of the present invention. The bone fastener assembly 10 includes the bone screw 12 having a screw head 14 connected to a shank 16 extending to a tapered tip 18. The screw head 14 includes a first longitudinal member aperture 20 designed and proportioned to secure a first longitudinal member 22 and a second longitudinal member aperture 26 designed and proportioned to secure a second longitudinal member 28.

The first compression member 24 includes a first set of compression member threads (not shown) that mate to a first set of compression aperture threads (not shown) with complimentary thread pitch, spacing and/or size to secure the first compression member 24 within the first longitudinal member aperture 20. The first compression member 24 secures the first longitudinal member 22 within the first longitudinal member aperture 20. The first compression member 24 includes a fitting 50 about the top that corresponds to an insertion tool used to insert, remove, adjust, tighten or loosen the first compression member 24. The fitting may be a socket head, slotted fitting, Phillips fitting, Pozidriv fitting, Torx fitting, hex fitting, Robertson fitting, tri-wing fitting, Torq-set fitting, spanner fitting or specialized fitting. The first compression member 24 may be inserted and tightened to the appropriate position, and may protrude above the screw head 14, be recessed below the screw head 14 or be substantially flush with the screw head 14. In addition, the first compression member bottom surface (not shown) may have a flat shape, a pointed shape, a rounded shape (e.g., concave or convex), a polygonal shape, free-formed shape or a combination thereof. The first compression member bottom surface (not shown) may be constructed from or coated with a malleable substance capable of deforming upon contact with the first longitudinal member 22.

The screw head 14 also includes a second longitudinal member aperture 26 designed and proportioned to fit a second longitudinal member 28 that is secured by a second compression member 30. The second compression member 30 extends through a second compression member aperture 32 and into the second longitudinal member aperture 26 to secure the second longitudinal member 28. The second compression member aperture 32 includes a second set of aperture treads (not shown) that mate to a second set of compression member threads (not shown) with complimentary thread pitch, spacing and/or size to secure the second compression member 30 within the second compression member aperture 32 and secure the second longitudinal member 28 within the second longitudinal member aperture 26. The second compression member 30 is positioned into the second longitudinal member aperture 26 and adjusted to extend through a second compression member aperture 32 to contact and secure the second longitudinal member 28 to the screw head 14. The second compression member 30 includes a second fitting 56 about the second compression member top surface 58 that corresponds to a tool (not shown) used to insert, remove, adjust, tighten or loosen the second compression member 30.

The shank 16 of the bone screw 12 includes a threaded portion 34 having shank threads 36 for attachment to the bone (e.g., spinal anatomy (not shown)). The shank 16 is designed to position the screw head 14 relative to the other components of the assembled device and the bones. The threaded portion 34 may be a helical groove, a thread formed on its surface or a segmented helical member having areas with and without the helical member (not shown). The pitch 42 and the spacing of the threads of the threaded portion 34 may be varied to allow for easier insertion and/or better adhesion to the bone (not shown). Alternatively, the shank 16 may include a non-grooved surface, a porous surface, a deformable surface, an undulating surface or other surface known to the skilled artisan. The bone screw 12 may have different threaded portion 34 lengths, diameter and/or pitch as necessary for a particular purpose, particular size of bone, particular subject age, particular density of bone, specific vertebra, etc. In addition, the tapered tip 18 may be sharp or blunt to allow better penetration into the bone (not shown).

Figure 6:
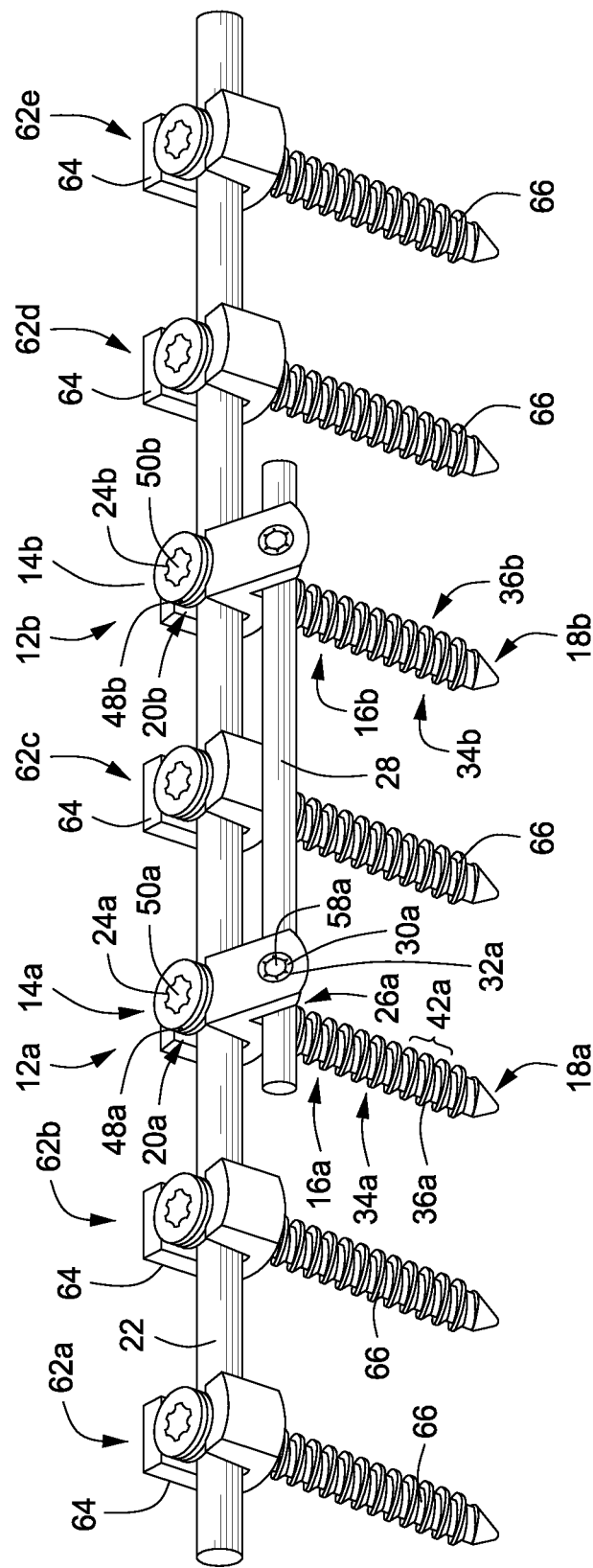
FIG. 6 illustrates a perspective view of a set of bone screw assemblies according to an embodiment of the invention.

Refer now to FIG. 6 there being shown a set of bone screw assemblies according to one embodiment of the present invention. FIG. 6 includes five screws 62A-62E connected to two bone screws 12A and 12B by a first longitudinal member 22 and a second longitudinal member 28.

The bone screw 12A includes a screw head 14A connected to a shank 16A extending to a tapered tip 18A. The screw head 14A includes a first longitudinal member aperture 20A designed and proportioned to secure a first longitudinal member 22 and a second longitudinal member aperture 26A designed and proportioned to secure a second longitudinal member 28.

The first compression member 24A includes a first set of compression member threads 48A that mate to a first set of compression aperture threads (not shown) and have a complimentary thread pitch, spacing and/or size. The first compression member 24A is secured within the first longitudinal member aperture 20A and in-turn secures the first longitudinal member 22 within the first longitudinal member aperture 20A. The first compression member 24A includes a first fitting 50A (i.e., a Torx fitting or hex fitting) about the top that corresponds to a fitting on an insertion tool (not shown) used to insert, remove, adjust, tighten or loosen the first compression member 24A. The first compression member 24A may be inserted and tightened to secure the first longitudinal member 22 to the appropriate position. The first compression member 24A may protrude above the screw head 14A, be recessed below the screw head 14A or be substantially flush with the screw head 14A. In addition, the first compression member bottom surface (not shown) may have a flat shape, a pointed shape, a rounded shape (e.g., concave or convex), a polygonal shape, or a combination thereof. The first compression member bottom surface (not shown) may also be constructed from or coated with a malleable substance capable of deforming upon contact with the first longitudinal member 22 or a textured surface to increase friction.

The screw head 14A also includes a second longitudinal member aperture 26A designed and proportioned to fit a second longitudinal member 28 that is secured by a second compression member 30A that extends through a second compression member aperture 32A and into the second longitudinal member aperture 26A to secure the second longitudinal member 28. The second compression member aperture 32A includes a second set of aperture treads (not shown) that mate to fit a second set of compression member threads (not shown). The compression member threads (not shown) and the second set of aperture treads (not shown) have complimentary thread pitch, spacing and/or size to secure the second compression member 30A within the second compression member aperture 32A and in-turn secure the second longitudinal member 28 within the second longitudinal member aperture 26A. The second compression member 30A is positioned into the second longitudinal member aperture 26A and adjusted to extend through a second compression member aperture 32A to contact and secure the second longitudinal member 28 to the screw head 14A. The second compression member 30A includes a second fitting (not shown) about the second compression member top surface 58A that corresponds to an insertion tool (not shown) used to insert, remove, adjust, tighten or loosen the second compression member 30A.

The shank 16A of the bone screw 12A includes a threaded portion 34A having shank threads 36A for securing the pedicle screw 12A to the spinal anatomy (not shown). The shank 16A is designed to position the screw head 14A relative to screws 62A-62E and bone screw 12B. The threaded portion 34A includes a helical groove formed on its surface. The pitch 42 and the spacing of the shank threads 36 may be varied to allow for easier insertion and/or better adhesion to the bone (not shown).

The bone screw 12B includes a screw head 14B connected to a shank 16B extending to a tapered tip 18B. The screw head 14B includes a first longitudinal member aperture 20B designed and proportioned to secure a first longitudinal member 22 and a second longitudinal member aperture 26B designed and proportioned to secure a second longitudinal member 28.

The first compression member 24B includes a first set of compression member threads 48B that mate to a first set of compression aperture threads (not shown) with complimentary thread pitch, spacing and/or size to secure the first compression member 24B within the first longitudinal member aperture 20B. The first longitudinal member 22 is secured within the first longitudinal member aperture 20B. The first compression member 24B includes a first fitting 50B (i.e., a Torx fitting or hex fitting) about the top that corresponds to a fitting on an insertion tool (not shown) used to insert, remove, adjust, tighten or loosen the first compression member 24B. The first compression member 24B may be inserted and tightened to the appropriate position, e.g., above the screw head 14B, below the screw head 14B or substantially flush with the screw head 14B. In addition, the first compression member bottom surface (not shown) may have a flat shape, a pointed shape, a rounded shape (e.g., concave or convex), a polygonal shape, or a combination thereof. The first compression member bottom surface (not shown) may be constructed from or coated with a malleable substance capable of deforming upon contact with the first longitudinal member 22.

The screw head 14B also includes a second longitudinal member aperture (not shown) designed and proportioned to fit a second longitudinal member 28. A second compression member (not shown) extends through a second compression member aperture (not shown) to the second longitudinal member aperture (not shown) to secure the second longitudinal member 28. The second compression member aperture (not shown) includes a second set of aperture treads (not shown) that mate to fit a second set of compression member threads (not shown). The compression member threads (not shown) and the second set of aperture treads (not shown) have complimentary thread pitch, spacing and/or size to secure the second compression member (not shown) within the second compression member aperture (not shown). The secured second compression member (not shown) in-turn secures the second longitudinal member 28 within the second longitudinal member aperture (not shown). The second compression member (not shown) is positioned within the second compression member aperture (not shown) and adjusted to extend through the second longitudinal member aperture (not shown) to contact and secure the second longitudinal member 28 to the screw head 14B. The second compression member (not shown) includes a second fitting (not shown) about the second compression member top surface (not shown) that corresponds to an insertion tool (not shown) used to insert, remove, adjust, tighten or loosen the second compression member (not shown).

The shank 16B includes a threaded portion 34B having shank threads 36B to secure the bone screw 12B to the spinal anatomy (not shown). The shank 16B is designed to position the screw head 14B relative to screws 62A-62E and bone screw 12A. In one example, the threaded portion 34B is a helical groove about the surface of the shank 16B.

The screws 62A-62E independently include a head 64 and a shank 66. The shank 66 includes threads to insert into the spinal anatomy (not shown) and positions the screw head 64. The screw head 64 allows the screws 62A-62E to connect to a first longitudinal member 22 and/or a second longitudinal member 28 for treatment.

Figure 7:
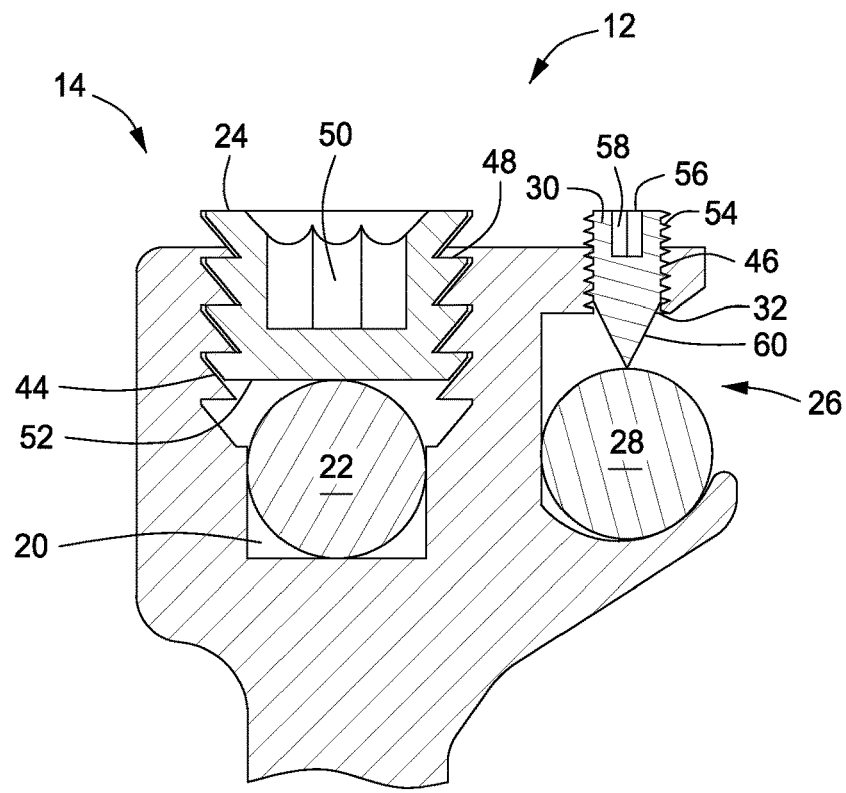
FIG. 7 illustrates a cross sectional view of the bone screw head according to one embodiment of the present invention.

FIG. 7 illustrates a cross sectional view of the pedicle screw head, generally designated by reference numeral 14, according to one embodiment of the present invention. The bone screw 12 includes a screw head 14 connected to a shank (not shown) extending to a tapered tip (not shown). The screw head 14 includes a first longitudinal member aperture 20 designed and proportioned to fit a first longitudinal member 22. A first compression member 24 also fits the first longitudinal member aperture 20 to secure the first longitudinal member 22. The first longitudinal member aperture 20 includes a first set of aperture threads 44 positioned about the first longitudinal member aperture 20 to accept the first compression member 24. The first compression member 24 includes a first fitting 50 (i.e., a Torx fitting or hex fitting) about the top that corresponds to an insertion tool (not shown). The first compression member 24 may be inserted and tightened to the appropriate position and may protrude above the screw head 14, be recessed below the screw head 14 or be substantially flush with the screw head 14.

The screw head 14 also includes a second longitudinal member aperture 26 designed and proportioned to fit a second longitudinal member 28. A second compression member 30 extends through a second compression member aperture 32 and into the second longitudinal member aperture 26 to secure the second longitudinal member 28. The second compression member aperture 32 includes a second set of aperture treads 46 positioned about the top of the screw head 14 that extends through the second compression member aperture 32 to the second longitudinal member aperture 26.

The present invention may be used to stabilize and position any bone. Generally, the bones stabilized by the present invention are vertebrae and include the spinous process of the vertebra, the transverse process of the vertebra, the pedicle of the vertebra, the posterior face of the vertebral lamina, the posterior arch of the vertebra or a combination thereof. The vertebra may be modified to accept the present invention, e.g., milling, grinding, removing segments of bone, installing plates, spacers, adaptors, fittings or combinations thereof. Furthermore, the present invention may be installed on each side of the spinous process in similar or different embodiments.

Figure 8A:
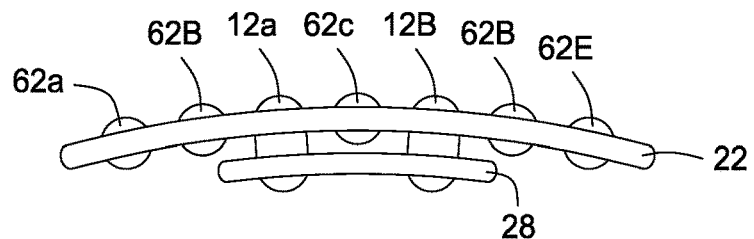
FIGS. 8A and 8B illustrate top views of sets of bone screw assemblies according to the present invention.
Figure 8B:
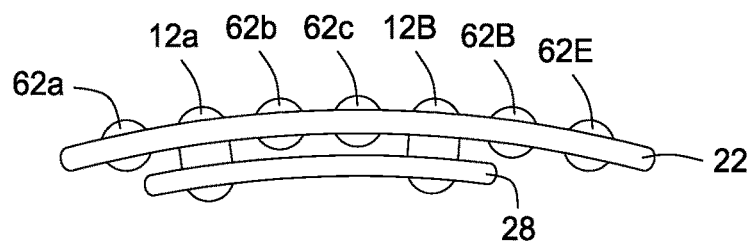

FIGS. 8A and 8B illustrate top views of sets of bone screw assemblies according to the present invention. FIG. 8 includes five bone screws 62A-62E connected to two bone screws 12A and 12B by a first longitudinal member 22 and a second longitudinal member 28. The first longitudinal member 22 and second longitudinal member 28 are shown with a bend or arc from bone screw 62A to bone screw 62E. The curve may be gradual, progressive or free-formed as necessary for the specific procedure. FIG. 8A illustrates top view of a bone screw assembly according to the present invention that is used to augment the apex segments. FIG. 8B illustrates top view of a bone screw assembly according to the present invention that is used to augment the apical/caundal segments.

Figure 9A:
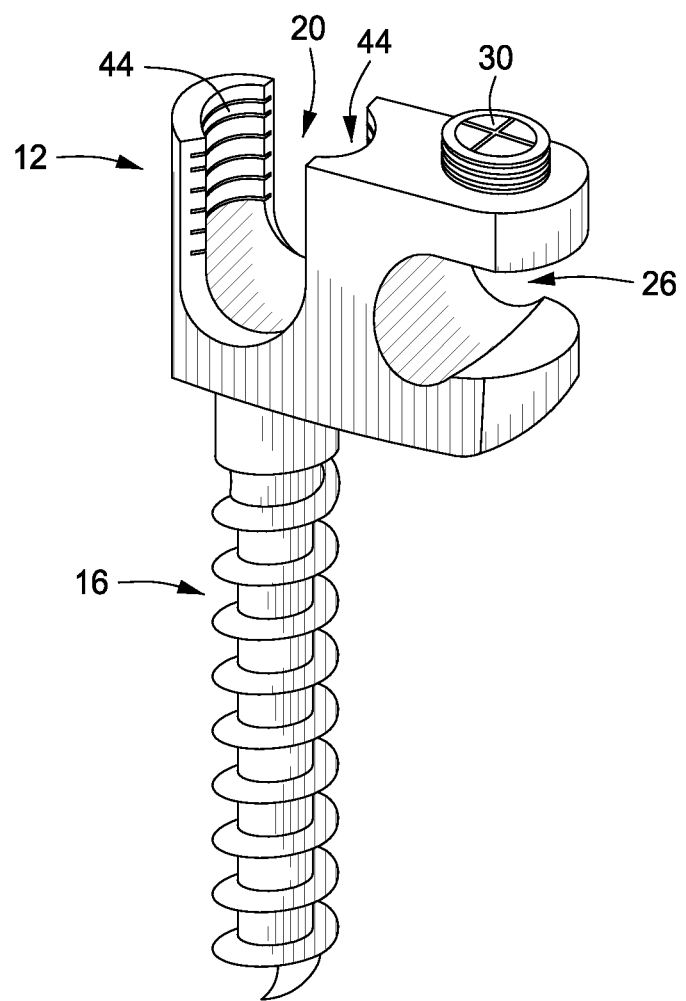
FIG. 9A illustrates a perspective view of one embodiment of the bone screw.

FIG. 9A illustrates a perspective view of the pedicle screw 12 having a screw head 14 connected to a non-grooved shank 16 extending to a tapered tip (not shown). The screw head 14 includes a first longitudinal member aperture 20 designed and proportioned to fit a first longitudinal member (not shown). The first longitudinal member aperture 20 includes a first set of aperture threads 44 positioned about the first longitudinal member aperture 20 to accept the first compression member (not shown). The screw head 14 also includes a second longitudinal member aperture 26 designed and proportioned to fit a second longitudinal member (not shown). A second compression member 30 extends through a second compression member aperture (not shown) and into the second longitudinal member aperture 26 to secure the second longitudinal member (not shown).

Figure 9B:
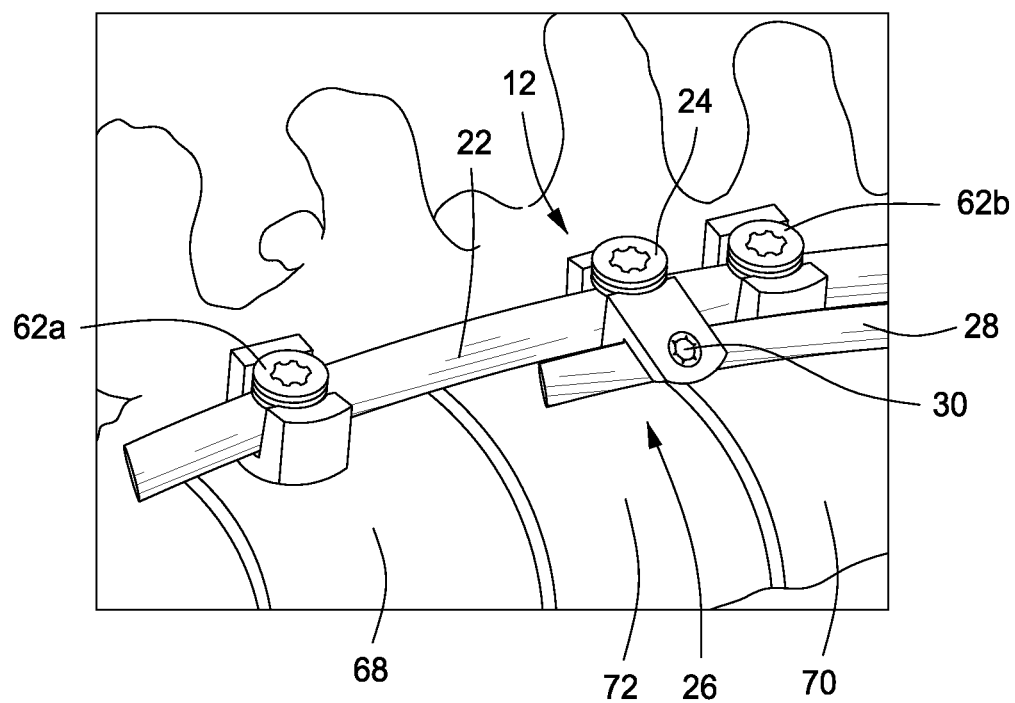
FIGS. 9B to 9G illustrate perspective views of the bone screw in context of a set of bone screw assemblies according to the present invention.

FIG. 9B includes two bone screws 62A-62B connected to a bone screw 12 by a first longitudinal member 22 and a second longitudinal member 28. The first longitudinal member 22 and second longitudinal member 28 are shown with a bend or arc from bone screw 62A to bone screw 62B. The bone screws 62A and 62B are connected to a first vertebra 68 and a third vertebra 70. The bone screw 12 is attached to a second vertebra 72. The assembly connects the first vertebra 68, the second vertebra 72 and the third vertebra 70 through the first longitudinal member 22 and the second longitudinal member 28. The first longitudinal member aperture 20 accepts the first longitudinal member 22 and is secured by the first compression member 24. The screw head 14 also includes a second longitudinal member aperture 26 designed and proportioned to fit a second longitudinal member 28. The second longitudinal member 28 is secured by a second compression member 30 extending through a second compression member aperture (not shown) and into the second longitudinal member aperture 26. The shank (not shown) of the bone screw 12 and bone screw 62A extend into the respective vertebrae.

Figure 9C:
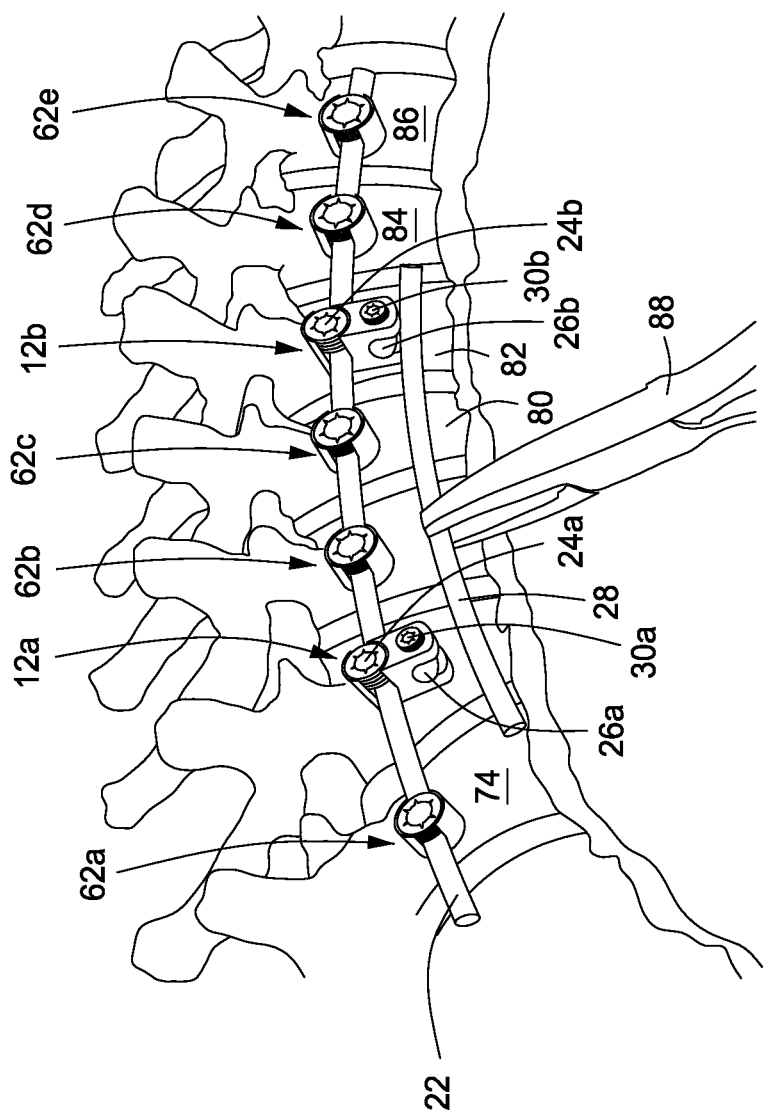

FIG. 9C includes five bone screws 62A-62E connected to bone screws 12A and 12B by a first longitudinal member 22. A second longitudinal member 28 is being positioned by the tool 88 to connect bone screw 12A and bone screw 12B. The bone screw 12A includes a first longitudinal member aperture 20A that accepts the first longitudinal member 22 and is secured by the first compression member 24A. The bone screw 12A also includes a second longitudinal member aperture 26A designed and proportioned to fit a second longitudinal member 28. The second longitudinal member 28 is secured by a second compression member 30A extending through a second compression member aperture (not shown) and into the second longitudinal member aperture 26A.

Similarly, the bone screw 12B includes a first longitudinal member aperture 20B that accepts the first longitudinal member 22 and is secured by the first compression member 24B. The bone screw 12B also includes a second longitudinal member aperture 26B designed and proportioned to fit a second longitudinal member 28. The second longitudinal member 28 is secured by a second compression member 30B extending through a second compression member aperture (not shown) and into the second longitudinal member aperture 26B.

The five bone screws 62A-62E are secured in the respective vertebrae 74, 78, 80, 84 and 86, while bone screw 12A is anchored to vertebra 76 and bone screw 12B is anchored to vertebra 82. The first longitudinal member 22 and second longitudinal member 28 are shown with a bend, curve or arc from bone screw 62A to bone screw 62E. The assembly connects the first vertebra 74 to the last vertebra 86 through the first longitudinal member 22. The vertebrae 76 through 82 are further supported by the second longitudinal member 28 that is connected to the bone screw 12A and the bone screw 12B.

Figure 9D:
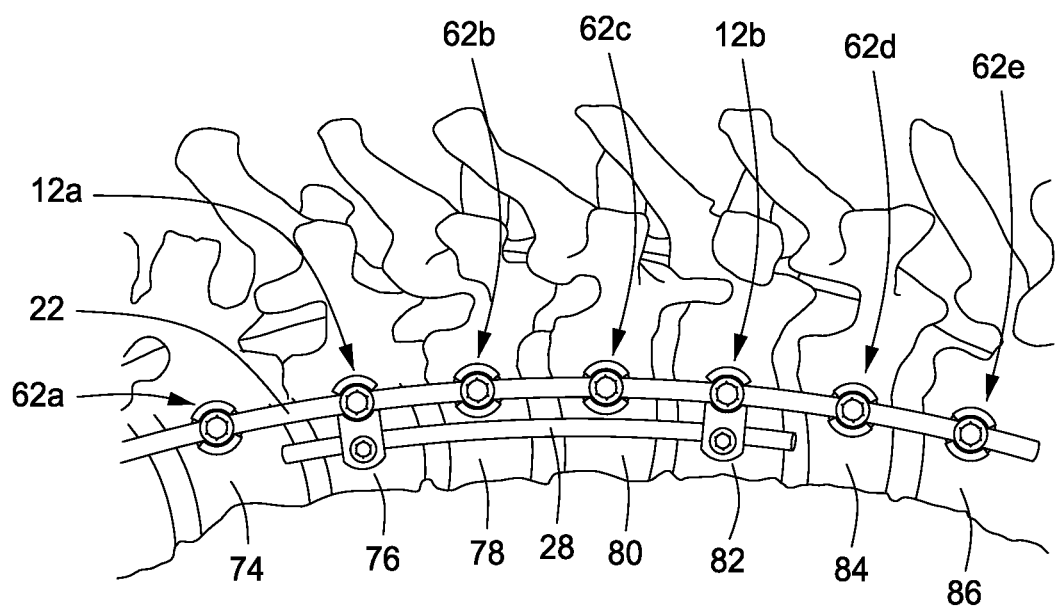

FIG. 9D includes five bone screws 62A-62E connected to bone screws 12A and 12B by a first longitudinal member 22 and a second longitudinal member 28. The five bone screws 62A-62E are secured in the respective vertebrae 74, 78, 80, 84 and 86, while bone screw 12A is anchored to vertebra 76 and bone screw 12B is anchored to vertebra 82. The first longitudinal member 22 and second longitudinal member 28 are shown with a bend, curve or arc from bone screw 62A to bone screw 62E. The assembly connects the first vertebra 74 to the last vertebra 86 through the first longitudinal member 22. The vertebrae 76 through 82 are further supported by the second longitudinal member 28 that is connected to the bone screw 12A and the bone screw 12B.

Figure 9E:
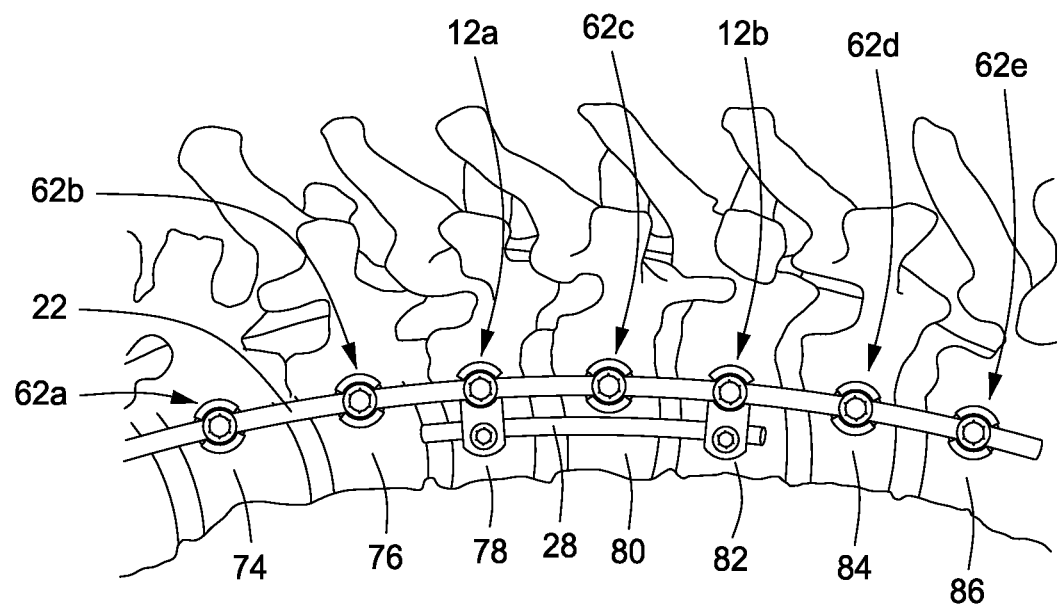

FIG. 9E includes five bone screws 62A-62E connected to bone screws 12A and 12B by a first longitudinal member 22 and a second longitudinal member 28. The five bone screws 62A-62E are secured in the respective vertebrae 74, 76, 80, 84 and 86, while bone screw 12A is anchored to vertebra 78 and bone screw 12B is anchored to vertebra 82. The first longitudinal member 22 and second longitudinal member 28 are shown with a bend, curve or arc from bone screw 62A to bone screw 62E. The assembly connects the first vertebra 74 to the last vertebra 86 through the first longitudinal member 22. The vertebrae 76 through 82 are further supported by the second longitudinal member 28 that is connected to the bone screw 12A and the bone screw 12B.

Figure 9F:
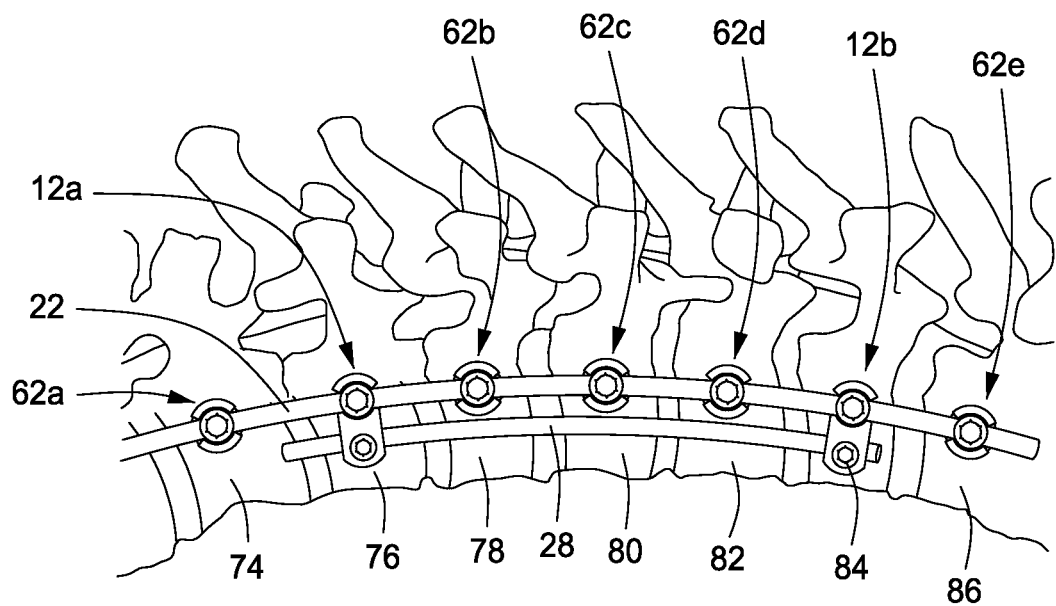

FIG. 9F includes five bone screws 62A-62E connected to bone screws 12A and 12B by a first longitudinal member 22 and a second longitudinal member 28. The five bone screws 62A-62E are secured in the respective vertebrae 74, 78, 80, 82 and 86, while bone screw 12A is anchored to vertebra 76 and bone screw 12B is anchored to vertebra 84. The first longitudinal member 22 and second longitudinal member 28 are shown with a bend, curve or arc from bone screw 62A to bone screw 62E. The assembly connects the first vertebra 74 to the last vertebra 86 through the first longitudinal member 22. The vertebrae 76 through 84 are further supported by the second longitudinal member 28 that is connected to the bone screw 12A and the bone screw 12B.

Figure 9G:
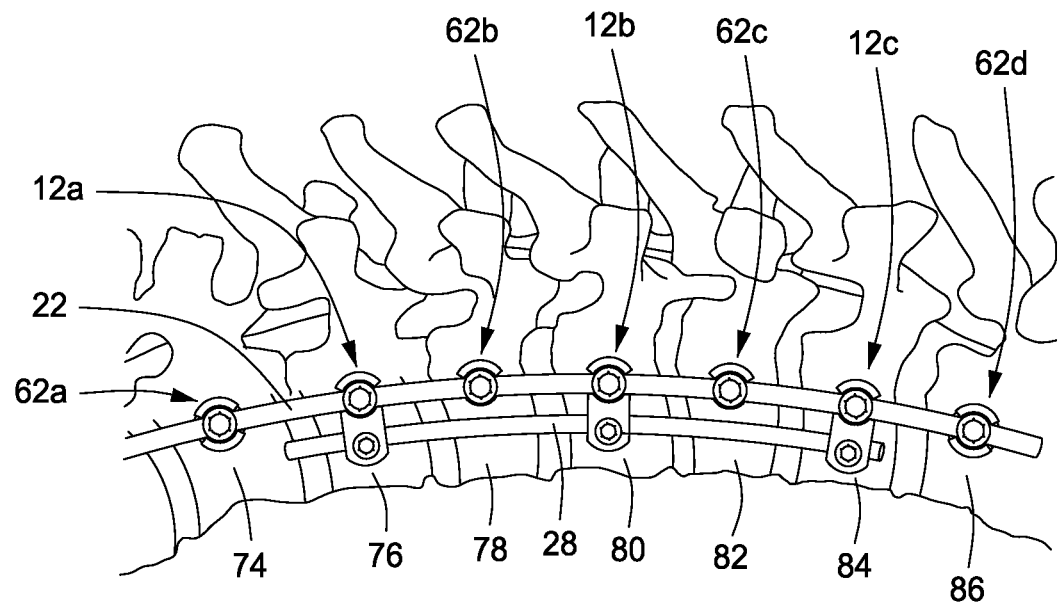

FIG. 9G includes four bone screws 62A-62D connected to bone screws 12A, 12B and 12C by a first longitudinal member 22 and a second longitudinal member 28. The four bone screws 62A-62D are secured in the respective vertebrae 74, 78, 82 and 86, while bone screw 12A is anchored to vertebra 76, bone screw 12B is anchored to vertebra 80 and bone screw 12C is anchored to vertebra 84. The first longitudinal member 22 and second longitudinal member 28 are shown with a bend, curve or arc from bone screw 62A to bone screw 62E. The assembly connects the first vertebra 74 to the last vertebra 86 through the first longitudinal member 22. The vertebrae 76 through 84 are further supported by the second longitudinal member 28 that is connected to the bone screw 12A, the bone screw 12B and the bone screw 12C.

The bone screws 12A and 12B each have a first longitudinal member aperture 20A/20B that accepts a first longitudinal member 22. The first longitudinal member 22 is secured by the first compression member 24A/24B. The bone screws 12A/12B each include a second longitudinal member aperture 26A/26B designed and proportioned to fit a second longitudinal member 28. A second compression member 30A/30B extends through a second compression member aperture (not shown) and into the second longitudinal member aperture 26A/26B to secure the second longitudinal member 28.

Figure 10A:
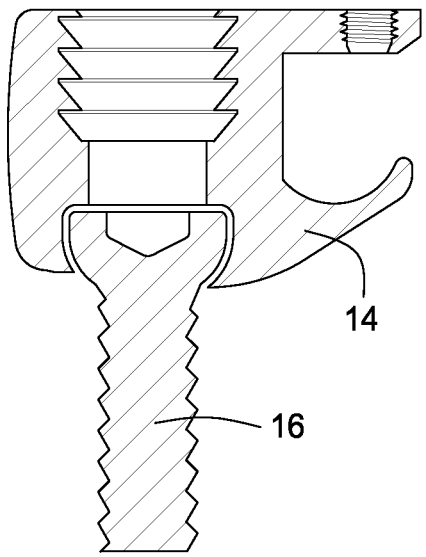
FIGS. 10A to 10D illustrate the screw is a polyaxial screw which can receive the rod at any direction.
Figure 10B:
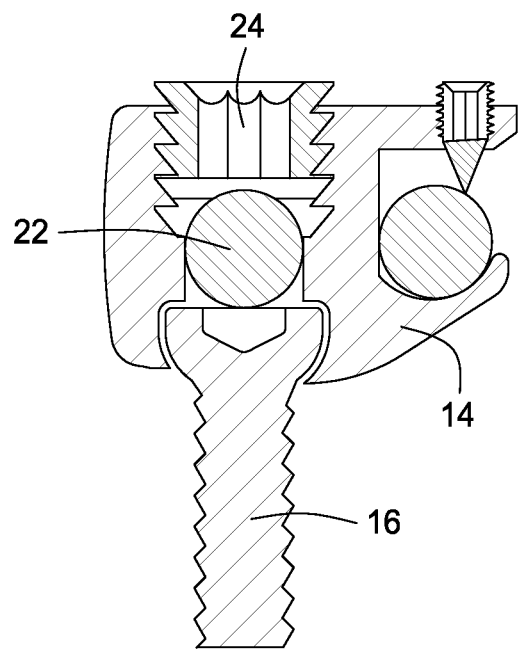
Figure 10C:
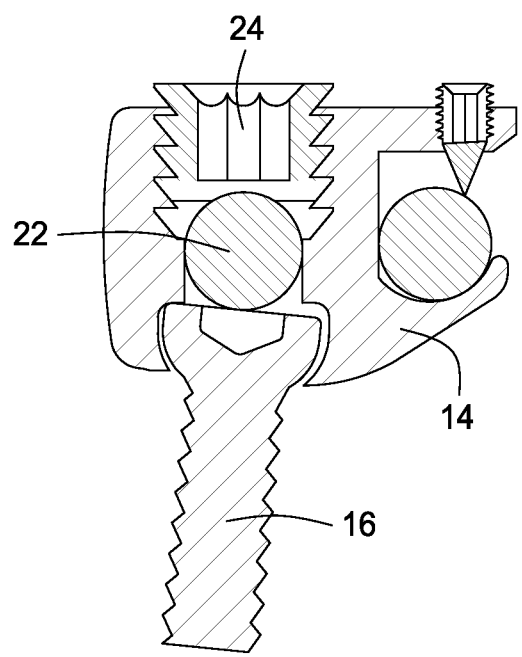
Figure 10D:
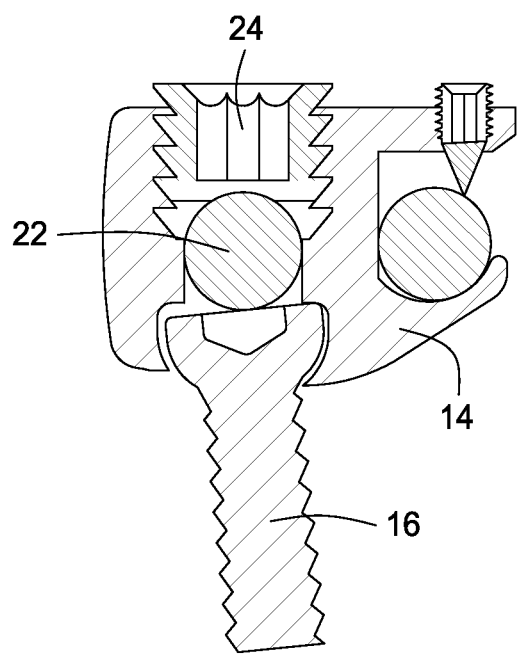

FIGS. 10A to 10D illustrate an embodiment of the present invention, wherein the screw is a polyaxial screw and can receive the rod at any direction. The screw may be made of, e.g., titanium, which is highly resistant to corrosion and fatigue, and is MRI compatible. In FIGS. 10A to 10D, the screw head 14 and the shank 16 are two separate parts or components. The shank 16 is threaded and the screw head 14 is mobile i.e., it swivels helping to defray vertebral stress. FIG. 10A is a cross section illustration of this embodiment without longitudinal member attachments (rods). FIG. 10B is a cross-section of such device with longitudinal member attachments (rods); the shank 16 in FIG. 10B demonstrates straight alignment. FIG. 10C shows the shank 16 with an angled alignment towards one direction (left). FIG. 10D shows the shank 16 with an angled alignment towards another direction (right). In certain embodiments, the first longitudinal member 22 may act as a contact cushion to stabilize the screw head 14, the first compression member 24 and the shank 16. The cushioning force may depend on the material and the shape of the longitudinal member attachments 22 (i.e. rods or elongated rectangle), and how deep the first compression member 24 is screwed in.

Figure 11A:
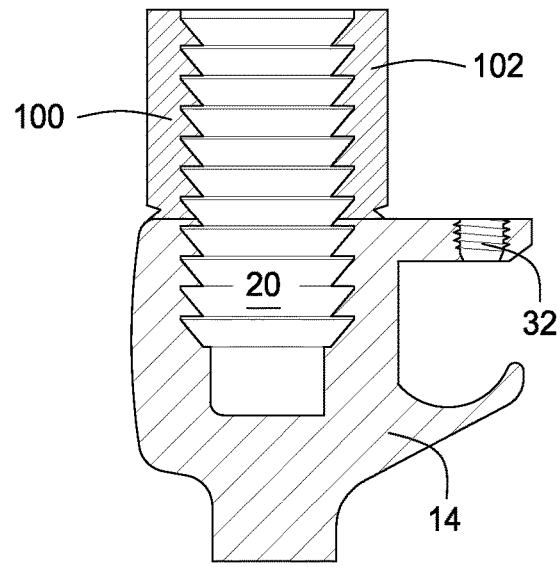
FIGS. 11A to 11D illustrate the screw is a reduction screw which has long arms to receive the rod and has a reduction function.
Figure 11B:
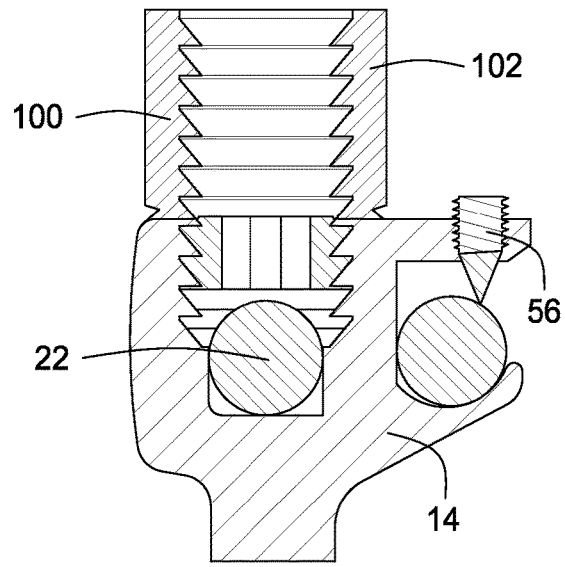
Figure 11C:
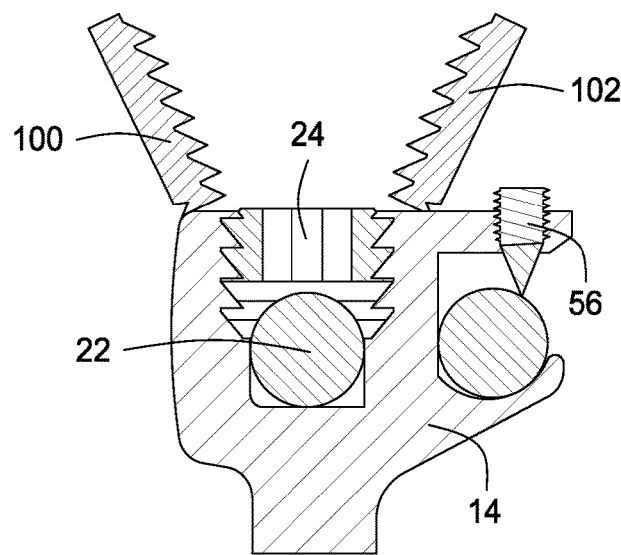
Figure 11D:
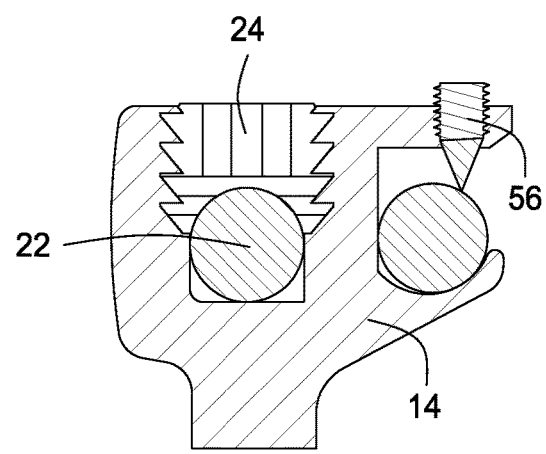

FIGS. 11A to 11D illustrate the screw as a reduction screw, which has two long arms to assist the reception and alignment of the first longitudinal member attachment (rod) 22 and has a reduction function, in this embodiment show as including internal threading. The first arm 100 and the second arm 102 may be threaded inside, and both arms may be broken off with gentle force (i.e., by hand or by hand using small tools) as shown in FIG. 11C resulting in an apparatus without the two long arms as shown in FIG. 11D. In another embodiment, the first and second arms 100 and 102 may be one circular hollow rod, with or without internal threads, with dimensions matching the first longitudinal member aperture 20 on top of the screw head 14. Both first and second arms 100 and 102 may also assist the reception and alignment of the first compression member 24. Similar arms may also be present for the second compression member aperture 32 on top of screw head 14 to assist the reception of the second fitting 56.

In certain embodiments, the apparatus of the present invention may act as pedicle screws typically used for spinal surgery. A pedicle screw is a type of bone screw designed for implantation into a vertebral pedicle. These screws are used to correct deformity, and/or treat trauma. Similar to other bone screws, pedicle screws may be used in instrumentation procedures to affix rods and plates to the spine. The screws may also be used to immobilize part of the spine to assist fusion by holding bony structures together.

In certain embodiments, the present invention provides an apparatus acting as pedicle screws, and methods to use such apparatus for the posterior approach in spinal surgery. The posterior approach is done from the back of a patient. With a posterior approach, an incision is made in the middle of the lower back over the area of the spine that requires attention. The muscles are moved to the side so that the surgeon can see the backside of the vertebrae. Once the spine is visible, the lamina of the vertebra is removed to take pressure off the dura and nerve roots, and the apparatus of the present invention may be inserted and attached. This allows the apparatus to grab into the bone of the vertebral body, giving them a good solid hold on the vertebra. Once everything is bolted together and tightened, this creates a stiff metal frame that holds the vertebrae still so that healing can occur.

Additionally, the structure of the present invention may be scaled to treat patients of different statures (e.g., midgets, men, women, children, elderly, etc). The present invention may be used to treat patients of all ages, heights, weights, bone sizes, etc. The bone fastener assembly may be scaled larger or smaller as needed. Alternatively, the individual components of the bone fastener assembly may be scaled larger or smaller as needed. For example, the screw head 14 may be enlarged to accommodate a longitudinal member of a larger diameter; the shank 16 may be thicker or longer to position the longitudinal member. In addition to humans, the present invention may be adapted for use on animals, e.g., dogs, cats, horses, etc.

In addition, the present invention may be of various lengths, diameters and having differing numbers or orientations of slots and/or bores. Sets of washers, bolts, screws and nuts and washer-nut combinations as disclosed herein can also be provided. Further, tools such as wrenches, drills, drill bits, pliers, sockets and screwdrivers compatible with the parts of the implant system of the present invention may also be included. It will be appreciated that the parts of the present invention should be constructed of biocompatible materials such as stainless steel, titanium, titanium alloys, certain plastics, or other known materials, e.g., titanium, a titanium alloy, a metal, an alloy, a stainless steel, a steel, a composite, a polymer, a blend of polymers, carbon fiber, a plastic, a thermoplastic, a synthetic material or other material known to the skilled artisan. In addition, the material may be formed from one material and coated with another biocompatible material.

Additionally the present invention may include a polymeric coating layer on part or all of the surfaces that contain one or more bioactive substances, such as antibiotics, chemotherapeutic substances, angiogenic growth factors, substances for accelerating the healing of the wound, growth hormones, antithrombogenic agents, bone growth accelerators or agents, and the like.

The components of the present invention may be assembled in part or entirely external to the patient and then implanted. However, the components may be assembled incrementally as implanted into the patient. In some instances, specialized instruments may be necessary to install the components; however, a cannula, a drill, a screwdriver, a hammer, pliers, wrench or other tools commonly used in orthopedic surgery may be used. Specialized instruments includes drivers having a socket fitting, slotted fitting, Phillips fitting, Pozidriv fitting, Torx fitting, hex fitting, Robertson fitting, tri-wing fitting, torq-set fitting, spanner fitting or specialized fitting. The sized, shape and configuration of the fitting will mate to the corresponding fitting and be of a size appropriate for the torque application.

It is contemplated that any embodiment discussed in this specification can be implemented with respect to any method, kit, reagent, or apparatus of the invention, and vice versa. Furthermore, the apparatus of the invention can be used to achieve the methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the apparatus, kit and methods of this invention have been described in terms of certain preferred embodiments, it will be apparent to those of skill in the art that variations may be applied to the apparatus, kit and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A unitary bone fixation assembly that provides augmented support comprising:
    a screw having a screw head and a threaded shank wherein the screw head and the threaded shank are formed from a single entity;
    a first aperture positioned about the screw head adapted to receive a first longitudinal member, wherein the first aperture lines up over the threaded shank;
    the first longitudinal member is inserted into the first aperture from top;
    a first compression member that engages the first aperture to secure the first longitudinal member;
    a second aperture positioned about the screw head to receive a second longitudinal member having a rod diameter, wherein the second aperture has a first aperture end opening, a second aperture end opening, and a lateral aperture opening, wherein the first aperture end opening and the second aperture end opening are on opposite sides of the second aperture forming a lumen, wherein the lateral aperture opening connects the first aperture end opening and the second aperture end opening, is smaller than the rod diameter to provide lateral support to the second longitudinal member after being inserted into the second aperture, and includes a lip extending above a bottommost surface of the second aperture, and wherein the first aperture and the second aperture are of a single unitary construction about the screw head, wherein the second aperture is offset so that the second aperture does not line up over the threaded shank;
    the second longitudinal member is inserted into the second aperture from lateral side of the screw head through one of the first or second aperture end openings; and
    a second compression member that engages the second aperture to secure the second longitudinal member and provide augmented support,
    wherein the second compression member has a bottom surface configured to be malleable in order to deform upon contact with the second longitudinal member
    wherein a height of the second aperture is greater than the width of the second aperture.

2. The assembly of claim 1, wherein bottommost surface of the second aperture is contoured to correspond to an outer portion of the second longitudinal member.

3. The assembly of claim 1, wherein the second longitudinal member has a smaller diameter than the first longitudinal member.

4. The assembly of claim 1, wherein the second compression member is smaller than the first compression member.

5. A bone fixation assembly that provides augmented support comprising:
    a screw having a screw head and a threaded shank;
    a first aperture positioned about the screw head adapted to receive a first longitudinal member within an open top portion of the first aperture wherein the first aperture is located within the screw head over the threaded shank;
    a first compression member that engages the first aperture to secure the first longitudinal member;
    a second aperture positioned about the screw head adapted to receive a second longitudinal member within an open side portion of the second aperture, wherein the second longitudinal member has a rod diameter, wherein the second aperture has a first aperture end opening, a second aperture end opening, and a lateral aperture opening, wherein the first aperture end opening and the second aperture end opening are on opposite sides of the second aperture forming a lumen, wherein the lateral aperture opening connects the first aperture end opening and the second aperture end opening, is smaller than the rod diameter to provide lateral support to the second longitudinal member after being inserted into the second aperture, and includes a lip extending above a bottommost surface of the second aperture, wherein the second aperture does not line up over the threaded shank, and wherein the first aperture and the second aperture are of a single unitary construction about the screw head; and a second compression member that engages the second aperture to secure the second longitudinal member and provide augmented support, wherein the second compression member has a bottom surface configured to be malleable in order to deform upon contact with the second longitudinal member, wherein a height of the second aperture is greater than the width of the second aperture.

6. The apparatus of claim 5, further comprising one of: the first longitudinal member and the second longitudinal member.

7. The apparatus of claim 6, wherein the one of: the first longitudinal member and the second longitudinal member comprises one of: a wire, a tube, a solid tube, a square tube, a spring and a combination thereof.

8. The apparatus of claim 5, further comprising a first set of threads formed on an inner wall of the first aperture that mate to a complimentary first set of threads formed about the first compression member.

9. The apparatus of claim 8, wherein the first set of threads and the complimentary first set of threads comprise a saw-tooth pitch in order to prevent a plug from loosening when clamped against the first longitudinal member.

10. The apparatus of claim 5, further comprising a threaded compression member aperture extending from a top surface of the screw head into the second aperture and a second set of threads disposed about the second compression member that fit threadably in the threaded compression member aperture, which second set of threads are removable.

11. The apparatus of claim 5, further comprising one or more active agents applied about the bone fixation assembly.

12. An augmented bone fixation assembly comprising:

two or more bone screw assemblies to be inserted into two or more bones, wherein each of the two or more bone fixation assemblies comprises a threaded shank and a screw head comprising a first aperture able to receive a first longitudinal member within an open top portion of the first aperture wherein the first aperture is located within the screw head over the threaded shank, a first compression member that engages the first aperture to secure the first longitudinal member therein, a second aperture able to receive a second longitudinal member within an open side portion of the second aperture, wherein the second longitudinal member has a rod diameter, wherein the second aperture has a first aperture end opening, a second aperture end opening, and a lateral aperture opening, wherein the first aperture end opening and the second aperture end opening are on opposite sides of the second aperture forming a lumen, wherein the lateral aperture opening connects the first aperture end opening and the second aperture end opening, is smaller than the rod diameter to provide lateral support to the second longitudinal member after being inserted into the second aperture, and includes a lip extending above a bottommost surface of the second aperture, wherein the second aperture is offset from the first aperture and configured to not line up over the threaded shank, and wherein the first aperture and the second aperture are of a single unitary construction about the screw head, and a second compression member that engages the second aperture to secure the second longitudinal member therein;

a first longitudinal member that extends through the first aperture of each of the two or more bone fixation assemblies; and a second longitudinal member that extends through the second aperture of at least two of the two or more bone screw assemblies, wherein the second longitudinal member augments the support of the first longitudinal member, wherein the second compression member has a bottom surface configured to be malleable in order to deform upon contact with the second longitudinal member wherein a height of the second aperture is greater than the width of the second aperture.

13. The apparatus of claim 12, wherein one or more conventional bone screws are positioned between the two or more bone fixation assemblies and connected by the first longitudinal member, wherein each of the conventional bone screws comprise a screw having a screw head, a threaded shank, and a first aperture positioned about the screw head to receive the first longitudinal member.

14. The apparatus of claim 12, wherein one of: the first longitudinal member and the second longitudinal member comprises one of: a wire, a tube, a solid tube, a square tube, a spring and a combination thereof.

15. The apparatus of claim 12, further comprising a first set of threads formed on an inner wall of the first aperture that mate to a complimentary first set of threads formed about the first compression member.

16. The apparatus of claim 12, wherein the first set of threads and the complimentary first set of threads comprise a saw-tooth pitch in order to prevent the plug from loosening when clamped against the first longitudinal member.

17. The apparatus of claim 12, further comprising a threaded compression member aperture extending from a top surface of the screw head into the second aperture and a second set of threads disposed about the second compression member that fit threadably in the threaded compression member aperture, which second set of threads are removable.

18. A bone fixation assembly kit having augmented support comprising:

two or more bone fixation assemblies, wherein each of the two or more bone fixation assemblies comprises a threaded shank and a screw head comprising a first aperture adapted to receive a first longitudinal member within an open top portion of the first aperture wherein the first aperture is located within the screw head over the threaded shank, a first compression member that engages the first aperture to secure the first longitudinal member therein, a second aperture adapted to receive a second longitudinal member within an open side portion of the second aperture, wherein the second longitudinal member has a rod diameter, wherein the second aperture has a first aperture end opening, a second aperture end opening, and a lateral aperture opening, wherein the first aperture end opening and the second aperture end opening are on opposite sides of the second aperture forming a lumen, wherein the lateral aperture opening connects the first aperture end opening and the second aperture end opening, is smaller than the rod diameter to provide lateral support to the second longitudinal member after being inserted into the second aperture, and includes a lip extending above a bottommost surface of the second aperture, wherein the second aperture does not line up over the threaded shank, and wherein the first aperture and the second aperture are of a single unitary construction about the screw head, and a second compression member that engages the second aperture to secure the second longitudinal member therein;

a first longitudinal member to extend through the first aperture of the two or more bone fixation assemblies; and a second longitudinal member to extend through the second aperture of at least two of the two or more bone fixation assemblies, wherein each of the bone fixation assemblies are polyaxial screws, wherein each screw head is disposed at a bottom portion of the first aperture, and wherein the first aperture is configured to swivel in relation to each bone screw assembly to defray vertebral stress wherein the second compression member has a bottom surface configured to be malleable in order to deform upon contact with the second longitudinal member wherein a height of the second aperture is greater than the width of the second aperture.

19. The kit of claim 18, wherein one or more conventional bone screws are positioned between the two or more bone fixation assemblies and connected by the first longitudinal member, wherein each of the conventional bone screws comprise a screw having a screw head, a threaded shank, and a first aperture positioned about the screw head to receive the first longitudinal member.

* * * * *